(12) United States Patent
Xiao et al.

(10) Patent No.: US 10,907,163 B1
(45) Date of Patent: Feb. 2, 2021

(54) APTAMERS THAT BIND TO NATURAL AND SYNTHETIC CANNABINOIDS

(71) Applicants: Yi Xiao, Miami, FL (US); Haixiang Yu, Durham, NC (US)

(72) Inventors: Yi Xiao, Miami, FL (US); Haixiang Yu, Durham, NC (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 16/901,723

(22) Filed: Jun. 15, 2020

(51) Int. Cl.
*C12N 15/11* (2006.01)
*C12N 15/115* (2010.01)
*G01N 33/94* (2006.01)
*G01N 21/64* (2006.01)

(52) U.S. Cl.
CPC ....... *C12N 15/115* (2013.01); *G01N 21/6428* (2013.01); *G01N 33/94* (2013.01); *C12N 2310/16* (2013.01); *C12N 2310/3517* (2013.01); *G01N 2021/6434* (2013.01); *G01N 2021/6439* (2013.01)

(58) Field of Classification Search
CPC .................................................. C12N 15/115
See application file for complete search history.

(56) References Cited

U.S. PATENT DOCUMENTS

2019/0017101 A1    1/2019 Jackson

OTHER PUBLICATIONS

Gawande, B.N., et al., "Selection of DNA Aptamers with Two Modified Bases." Proceedings of the National Academy of Sciences, 2017, 114(11): 2898-2903.
Hili, R., et al., "DNA Ligase-Mediated Translation of DNA Into Densely Functionalized Nucleic Acid Polymers." Journal of the American Chemical Society, 2013, 135: 98-101.
Jenison, R., et al., "High-Resolution Molecular Discrimination by RNA." Science, 1994, 263: 1425-1429.
Kimoto, M., et al., "Generation of High-Affinity DNA Aptamers Using an Expanded Genetic Alphabet." Nature Biotechnology, 2013, 31(5): 453-458.
Nakatsuka, N., et al., "Aptamer-Field-Effect Transistors Overcome Debye Length Limitations for Small-Molecule Sensing." Science, 2018, 362(6412): 319-324.
Rohloff, J.C., et al., "Nucleic Acid Ligands With Protein-Like Side Chains: Modified Aptamers and Their Use as Diagnostic and Therapeutic Agents." The American Society of Gene & Cell Therapy, 2014, 3(e201): 1-13.
Sefah, K., et al., "In Vitro Selection With Artificial Expanded Genetic Information Systems." Proceedings of the National Academy of Sciences, 2014, 111(4): 1449-1454.
Slavkovic, S., et al., "Isothermal Titration Calorimetry Studies of Aptamer-Small Molecule Interactions: Practicalities and Pitfalls." Aptamers, 2018, 2: 45-51.
Tuerk, C., et al., "Systematic Evolution of Ligands by Exponential Enrichment: RNA Ligands to Bacteriophage T4 DNA Polymerase." Science, 1990, 249(4968): 505-510.
Yang, K., et al., "High-Affinity Nucleic-Acid-Based Receptors for Steroids." ACS Chemical Biology, 2017, 12(12): 3103-3112.
Yang, K., et al., "In Vitro Selection and Amplification Protocols for Isolation of Aptameric Sensors for Small Molecules." Methods, 2016, 106: 58-65.
Yang, W., et al., "In Vitro Isolation of Class-Specific Oligonucleotide-Based Small-Molecule Receptors." Nucleic Acids Research, 2019, 47(12): 1-10.
Yu, H., et al., "In vitro isolation of small-molecule-binding aptamers with intrinsic dye-displacement functionality." Nucleic Acids Research, 2018, 46(8): 1-9.

*Primary Examiner* — Ekaterina Poliakova-Georgantas
(74) *Attorney, Agent, or Firm* — Saliwanchik, Lloyd & Eisenschenk

(57) ABSTRACT

The subject invention provides materials and methods for single-step detection of small molecules, e.g., natural and synthetic cannabinoids, in a sample. The subjection invention provides nucleic acids materials, e.g., aptamers (nucleic acid oligonucleotides) that can bind to natural and/or synthetic cannabinoids. The method for detecting a natural or synthetic cannabinoid in a sample comprises contacting the sample with an aptamer-based sensor selective for the natural or synthetic cannabinoid, and sensitively and rapidly detecting the natural or synthetic cannabinoid in the sample. The aptamer-based sensor comprises aptamers that can specifically binds to natural and/or synthetic cannabinoids with nanomolar dissociation constant.

17 Claims, 16 Drawing Sheets

Specification includes a Sequence Listing.

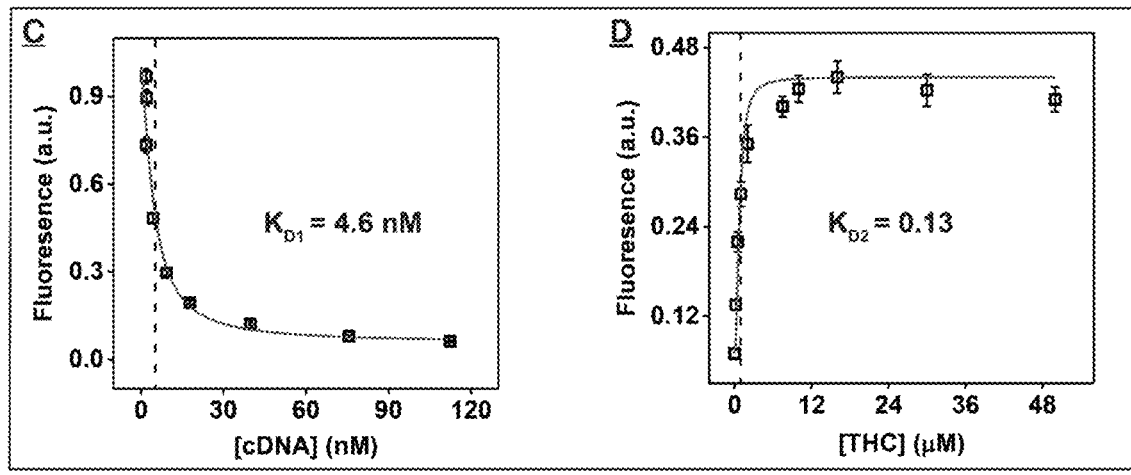
FIG. 4C
FIG. 4D
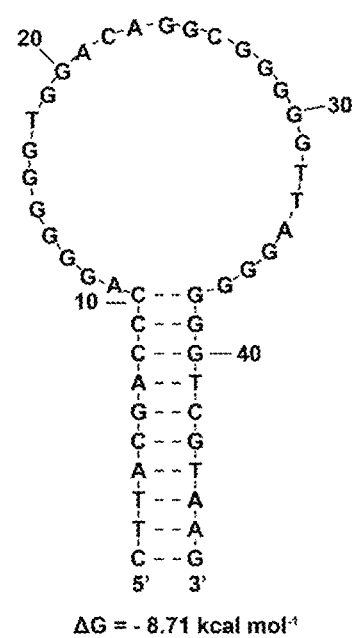
$\Delta G = -8.71$ kcal mol$^{-1}$
FIG. 5

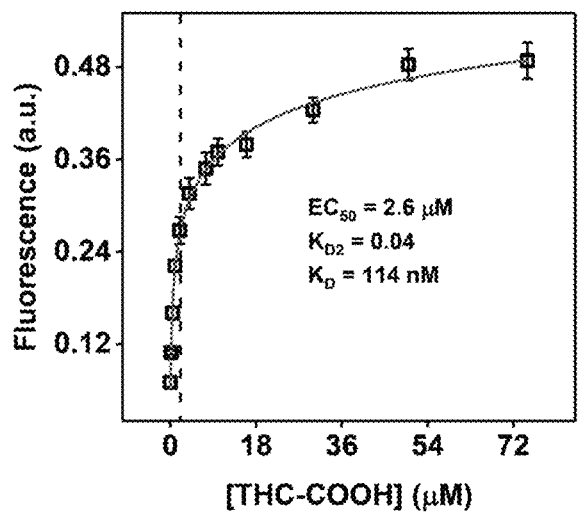
FIG. 6
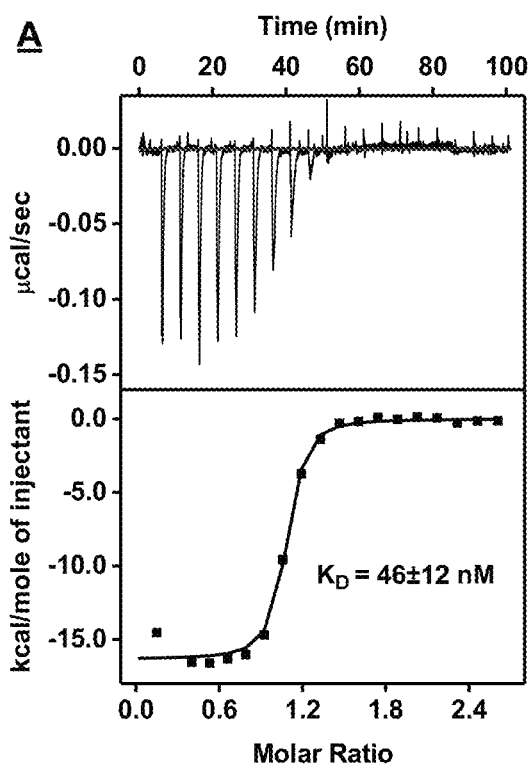
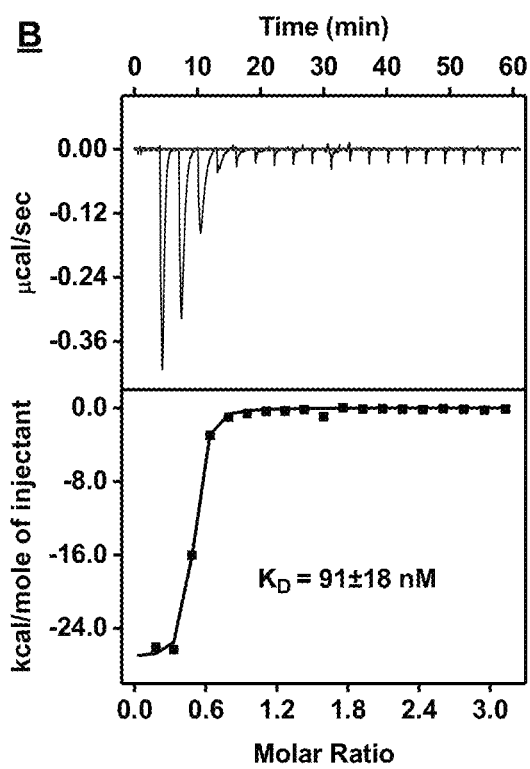
FIG. 7A  FIG. 7B

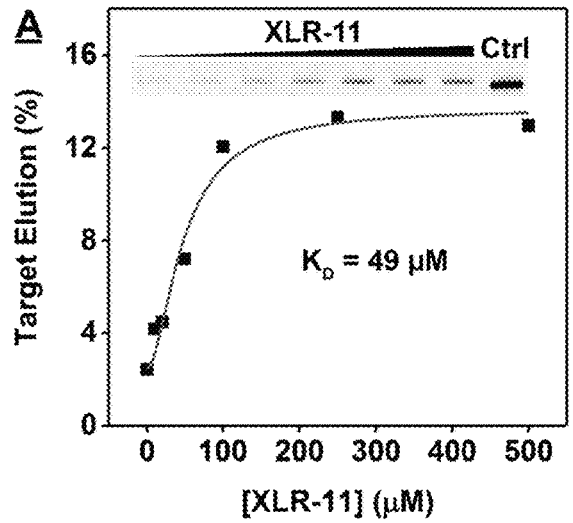 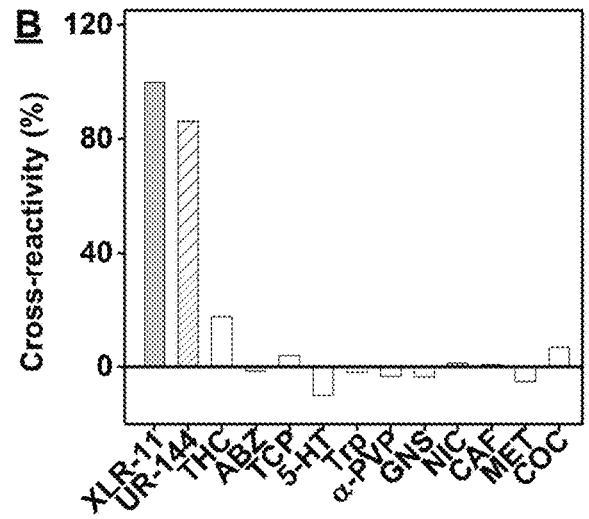
FIG. 11A  FIG. 11B
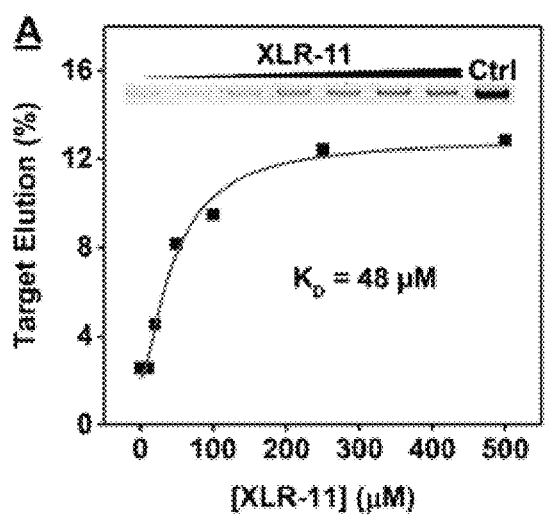 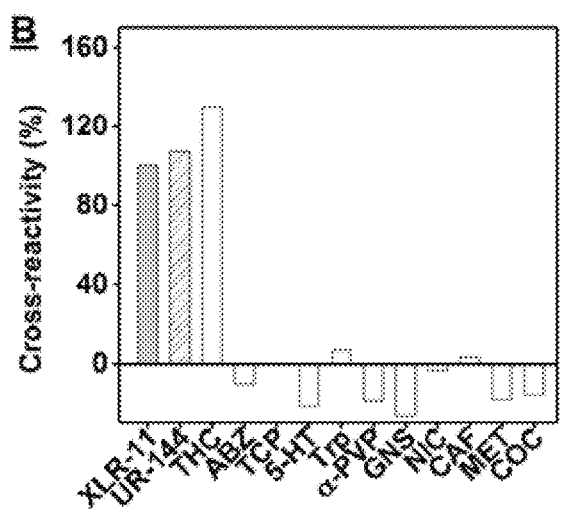
FIG. 12A  FIG. 12B

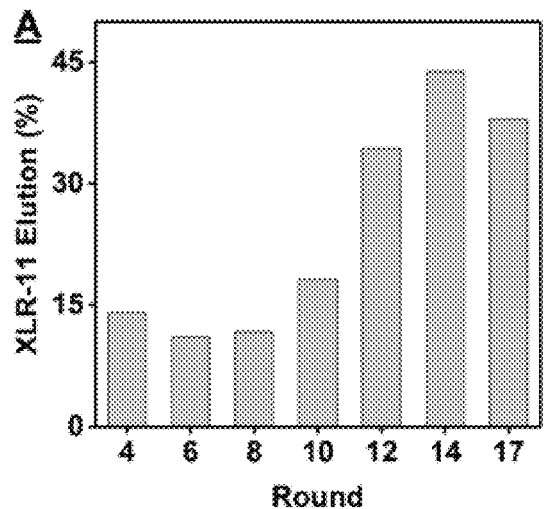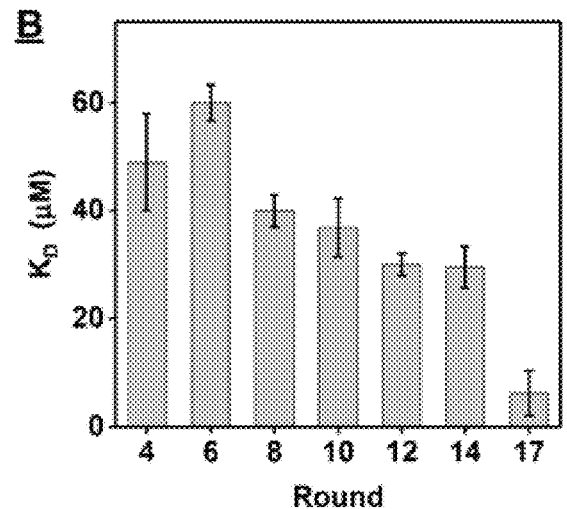
FIG. 13A                    FIG. 13B
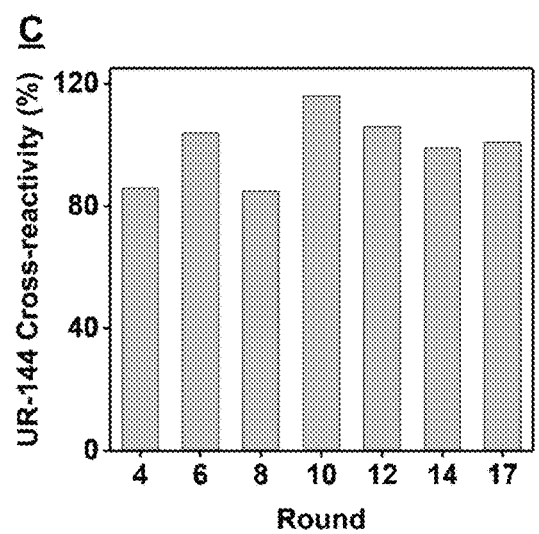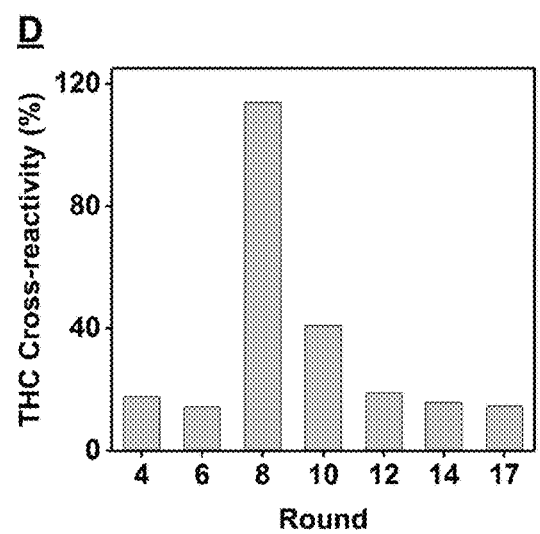
FIG. 13C                    FIG. 13D

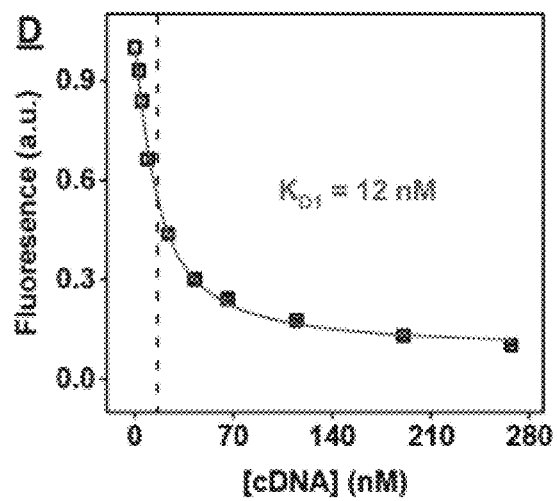
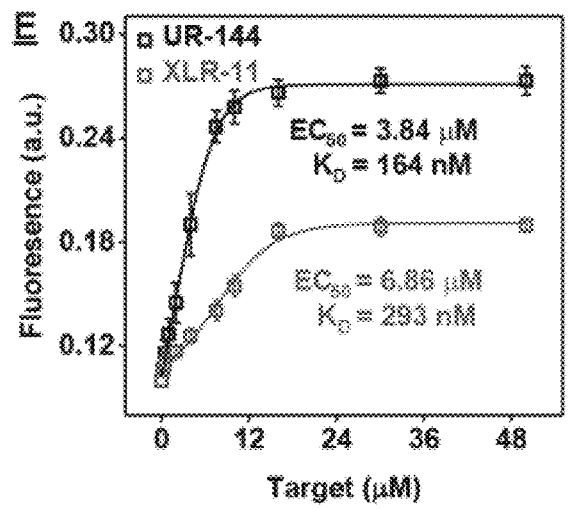
FIG. 14D
FIG. 14E
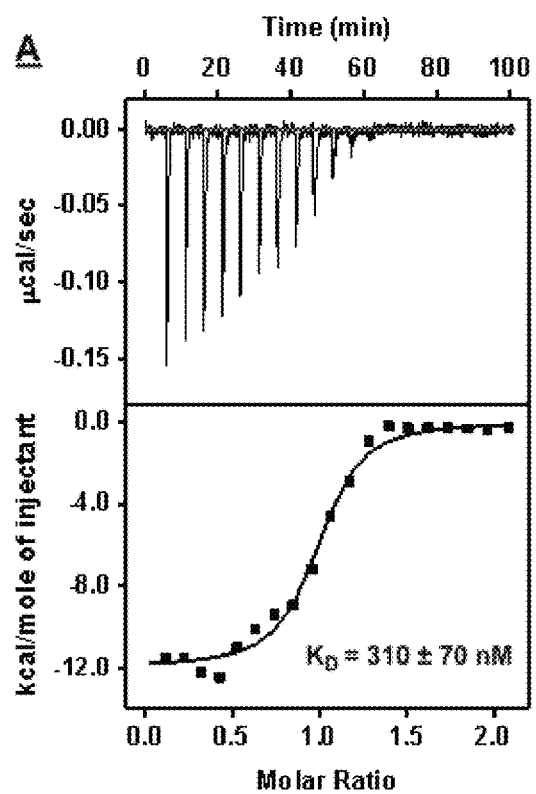
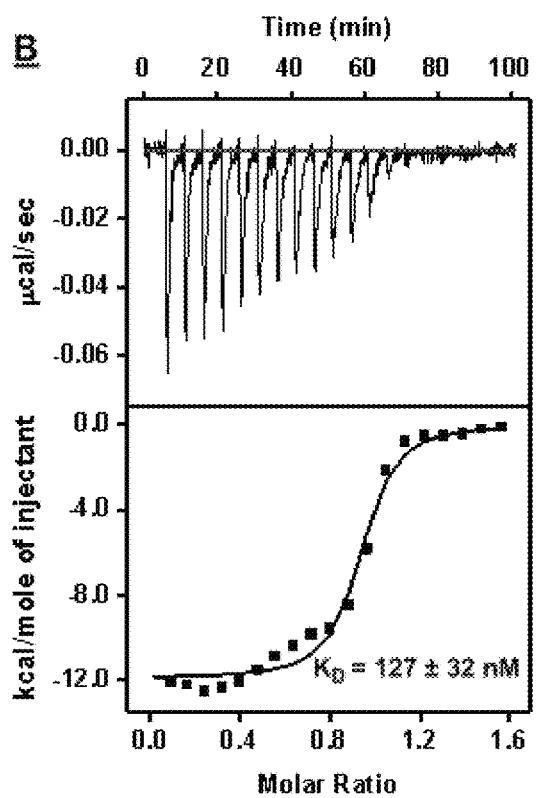
FIG. 15A
FIG. 15B

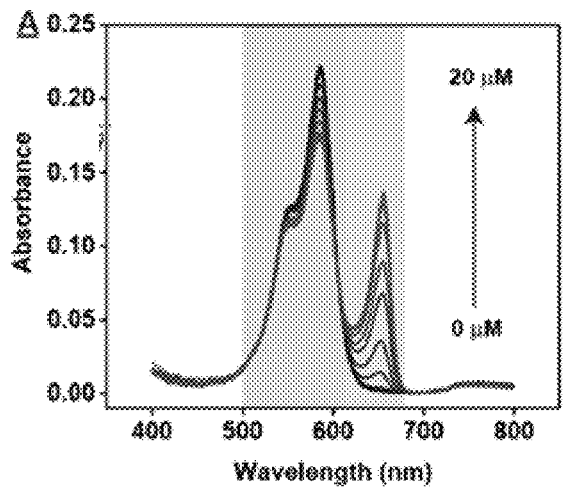
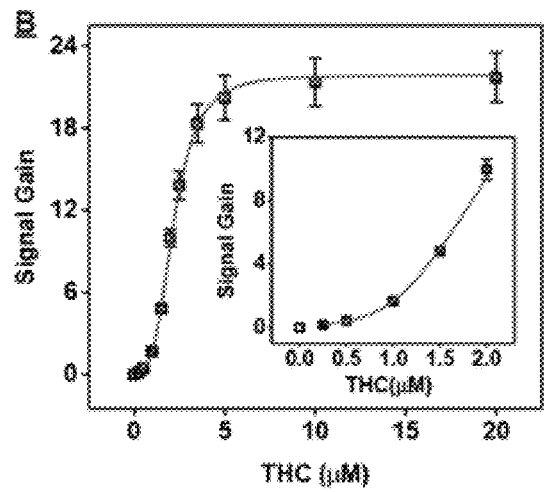
FIG. 18A  FIG. 18B
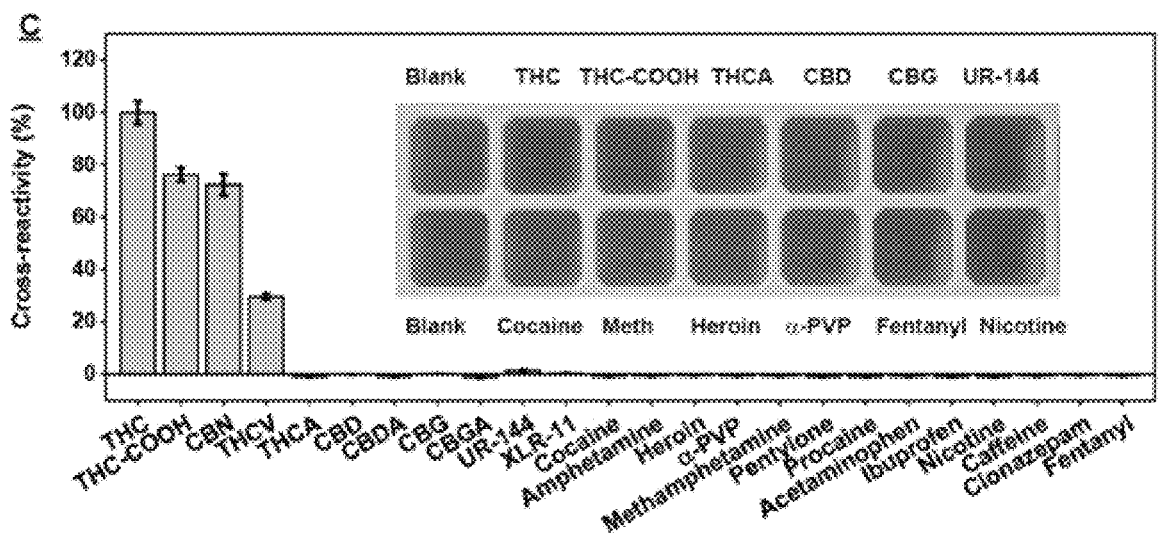
FIG. 18C

SEQUENCE LISTING

```
<160> NUMBER OF SEQ ID NOS: 26

<210> SEQ ID NO 1
<211> LENGTH: 25
<212> TYPE: DNA
<213> ORGANISM: Artificial sequence
<220> FEATURE:
<223> OTHER INFORMATION: aptamer
<220> FEATURE:
<221> NAME/KEY: misc_feature
<222> LOCATION: (25)..(25)
<223> OTHER INFORMATION: biotin modification

<400> SEQUENCE: 1
tttttgtcgt aagttctgcc atttt                                         25

<210> SEQ ID NO 2
<211> LENGTH: 73
<212> TYPE: DNA
<213> ORGANISM: Artificial sequence
<220> FEATURE:
<223> OTHER INFORMATION: aptamer
<220> FEATURE:
<221> NAME/KEY: misc_feature
<222> LOCATION: (24)..(53)
<223> OTHER INFORMATION: n is a, c, g, or t

<400> SEQUENCE: 2
cgagcatagg cagaacttac gacnnnnnnn nnnnnnnnnn nnnnnnnnnn nnngtcgtaa    60
```
gagcgagtca ttc                                                          73

<210> SEQ ID NO 3
<211> LENGTH: 47
<212> TYPE: DNA
<213> ORGANISM: Artificial sequence
<220> FEATURE:
<223> OTHER INFORMATION: aptamer

<400> SEQUENCE: 3
cttacgaccc aggggggtgg acaggcgggg gttaggggggg tcgtaag                    47

<210> SEQ ID NO 4
<211> LENGTH: 46
<212> TYPE: DNA
<213> ORGANISM: Artificial sequence
<220> FEATURE:
<223> OTHER INFORMATION: aptamer

<400> SEQUENCE: 4
cttacgactg tggtcgggtg gtgggcctct agagggtgt cgtaag                       46

<210> SEQ ID NO 5
<211> LENGTH: 46
<212> TYPE: DNA
<213> ORGANISM: Artificial sequence
<220> FEATURE:
<223> OTHER INFORMATION: aptamer

<400> SEQUENCE: 5
cttacgactg cgggcatttg tgggggggcgt cggtgggcgt cgtaag                     46

<210> SEQ ID NO 6
<211> LENGTH: 54
<212> TYPE: DNA
<213> ORGANISM: Artificial sequence
<220> FEATURE:
<223> OTHER INFORMATION: aptamer
<220> FEATURE:
<221> NAME/KEY: misc_feature
<222> LOCATION: (1)..(1)
<223> OTHER INFORMATION: Cy5 fluorophore modification

<400> SEQUENCE: 6
ggcagaactt acgacccagg ggggtggaca ggcgggggtt aggggggtcg taag             54

<210> SEQ ID NO 7
<211> LENGTH: 53
<212> TYPE: DNA
<213> ORGANISM: Artificial sequence
<220> FEATURE:
<223> OTHER INFORMATION: aptamer
<220> FEATURE:
<221> NAME/KEY: misc_feature
<222> LOCATION: (1)..(1)
<223> OTHER INFORMATION: Cy5 fluorophore modification

<400> SEQUENCE: 7
ggcagaactt acgactgtgg tcgggtggtg ggcctctaga ggggtgtcgt aag              53

<210> SEQ ID NO 8
<211> LENGTH: 14
<212> TYPE: DNA
<213> ORGANISM: Artificial
<220> FEATURE:
<223> OTHER INFORMATION: aptamer
<220> FEATURE:
<221> NAME/KEY: misc_feature

```
<222> LOCATION: (14)..(14)
<223> OTHER INFORMATION: Iowa Black RQ quencher modification

<400> SEQUENCE: 8
gtcgtaagtt ctgc                                                           14

<210> SEQ ID NO 9
<211> LENGTH: 30
<212> TYPE: DNA
<213> ORGANISM: Artificial sequence
<220> FEATURE:
<223> OTHER INFORMATION: aptamer

<400> SEQUENCE: 9 ccagggggt ggacaggcgg gggttagggg                                           30

<210> SEQ ID NO 10
<211> LENGTH: 30
<212> TYPE: DNA
<213> ORGANISM: Artificial sequence
<220> FEATURE:
<223> OTHER INFORMATION: aptamer

<400> SEQUENCE: 10 ccagggggt ggacagacgg gggttagggg                                           30

<210> SEQ ID NO 11
<211> LENGTH: 31
<212> TYPE: DNA
<213> ORGANISM: Artificial sequence
<220> FEATURE:
<223> OTHER INFORMATION: aptamer

<400> SEQUENCE: 11 ccagggggt ggacaggcgg ggggtcaggg g                                         31

<210> SEQ ID NO 12
<211> LENGTH: 31
<212> TYPE: DNA
<213> ORGANISM: Artificial sequence
<220> FEATURE:
<223> OTHER INFORMATION: aptamer

<400> SEQUENCE: 12
catgccgaca ccttccagaa ggttcagcgg a                                        31

<210> SEQ ID NO 13
<211> LENGTH: 30
<212> TYPE: DNA
<213> ORGANISM: Artificial sequence
<220> FEATURE:
<223> OTHER INFORMATION: aptamer

<400> SEQUENCE: 13
cgggctgtca actggggagt gcggactggt                                          30

<210> SEQ ID NO 14
<211> LENGTH: 30
<212> TYPE: DNA
<213> ORGANISM: Artificial sequence
<220> FEATURE:
<223> OTHER INFORMATION: aptamer

<400> SEQUENCE: 14
aactgaggcg gacagaaggg atccgcgtgg                                          30
```

```
<210> SEQ ID NO 15
<211> LENGTH: 30
<212> TYPE: DNA
<213> ORGANISM: Artificial sequence
<220> FEATURE:
<223> OTHER INFORMATION: aptamer

<400> SEQUENCE: 15
gcggctggag cgttaggtct caaggatagg                                      30

<210> SEQ ID NO 16
<211> LENGTH: 30
<212> TYPE: DNA
<213> ORGANISM: Artificial sequence
<220> FEATURE:
<223> OTHER INFORMATION: aptamer

<400> SEQUENCE: 16
gaggagacct accattgtga cggtaacgtt                                      30

<210> SEQ ID NO 17
<211> LENGTH: 30
<212> TYPE: DNA
<213> ORGANISM: Artificial sequence
<220> FEATURE:
<223> OTHER INFORMATION: aptamer

<400> SEQUENCE: 17
caccagtgag cctcccggga tcgtgaaatg                                      30

<210> SEQ ID NO 18
<211> LENGTH: 30
<212> TYPE: DNA
<213> ORGANISM: Artificial sequence
<220> FEATURE:
<223> OTHER INFORMATION: aptamer

<400> SEQUENCE: 18
acggataacc cacgtgtata ggttggagtg                                      30

<210> SEQ ID NO 19
<211> LENGTH: 30
<212> TYPE: DNA
<213> ORGANISM: Artificial sequence
<220> FEATURE:
<223> OTHER INFORMATION: aptamer

<400> SEQUENCE: 19
agggtagagc ctgatcaagt ggtgaattct                                      30

<210> SEQ ID NO 20
<211> LENGTH: 30
<212> TYPE: DNA
<213> ORGANISM: Artificial sequence
<220> FEATURE:
<223> OTHER INFORMATION: aptamer

<400> SEQUENCE: 20
ggcctgtgtg cggtcattga cgctggcgct                                      30

<210> SEQ ID NO 21
<211> LENGTH: 30
<212> TYPE: DNA
<213> ORGANISM: Artificial sequence
<220> FEATURE:
<223> OTHER INFORMATION: aptamer
```

-continued

<400> SEQUENCE: 21
tgcgtacgta aactgttttg tttgaccgta                                          30

<210> SEQ ID NO 22
<211> LENGTH: 30
<212> TYPE: DNA
<213> ORGANISM: Artificial sequence
<220> FEATURE:
<223> OTHER INFORMATION: aptamer

<400> SEQUENCE: 22
cggatcagca tacgttgcgt agtccaactg                                          30

<210> SEQ ID NO 23
<211> LENGTH: 30
<212> TYPE: DNA
<213> ORGANISM: Artificial sequence
<220> FEATURE:
<223> OTHER INFORMATION: aptamer

<400> SEQUENCE: 23
gttcggtaga gctagaattg tggcggtgac                                          30

<210> SEQ ID NO 24
<211> LENGTH: 30
<212> TYPE: DNA
<213> ORGANISM: Artificial sequence
<220> FEATURE:
<223> OTHER INFORMATION: aptamer

<400> SEQUENCE: 24
tgtggtcggg tggtgggcct ctagaggggt                                          30

<210> SEQ ID NO 25
<211> LENGTH: 30
<212> TYPE: DNA
<213> ORGANISM: Artificial sequence
<220> FEATURE:
<223> OTHER INFORMATION: aptamer

<400> SEQUENCE: 25
tgcgggcatt tgtgggggc gtcggtgggc                                           30

<210> SEQ ID NO 26
<211> LENGTH: 30
<212> TYPE: DNA
<213> ORGANISM: Artificial sequence
<220> FEATURE:
<223> OTHER INFORMATION: aptamer
<220> FEATURE:
<221> NAME/KEY: misc_feature
<222> LOCATION: (1)..(1)
<223> OTHER INFORMATION: n is c, g, a, or t
<220> FEATURE:
<221> NAME/KEY: misc_feature
<222> LOCATION: (2)..(2)
<223> OTHER INFORMATION: n is c, g, or a
<220> FEATURE:
<221> NAME/KEY: misc_feature
<222> LOCATION: (3)..(3)
<223> OTHER INFORMATION: n is a, g, c, or t
<220> FEATURE:
<221> NAME/KEY: misc_feature
<222> LOCATION: (4)..(4)
<223> OTHER INFORMATION: n is g, c, a, or t
<220> FEATURE:
<221> NAME/KEY: misc_feature
<222> LOCATION: (5)..(5)

```
<223> OTHER INFORMATION: n is g, t, a, or c
<220> FEATURE:
<221> NAME/KEY: misc_feature
<222> LOCATION: (6)..(6)
<223> OTHER INFORMATION: n is g, a, t, or c
<220> FEATURE:
<221> NAME/KEY: misc_feature
<222> LOCATION: (7)..(7)
<223> OTHER INFORMATION: n is g, a, t, or c
<220> FEATURE:
<221> NAME/KEY: misc_feature
<222> LOCATION: (8)..(8)
<223> OTHER INFORMATION: n is g, a, or c
<220> FEATURE:
<221> NAME/KEY: misc_feature
<222> LOCATION: (9)..(9)
<223> OTHER INFORMATION: n is g, c, a, or t
<220> FEATURE:
<221> NAME/KEY: misc_feature
<222> LOCATION: (10)..(10)
<223> OTHER INFORMATION: n is t, a, c, or g
<220> FEATURE:
<221> NAME/KEY: misc_feature
<222> LOCATION: (11)..(11)
<223> OTHER INFORMATION: n is g, c, or a
<220> FEATURE:
<221> NAME/KEY: misc_feature
<222> LOCATION: (12)..(12)
<223> OTHER INFORMATION: n is g, c, or a
<220> FEATURE:
<221> NAME/KEY: misc_feature
<222> LOCATION: (13)..(13)
<223> OTHER INFORMATION: n is a, c, or t
<220> FEATURE:
<221> NAME/KEY: misc_feature
<222> LOCATION: (14)..(14)
<223> OTHER INFORMATION: n is c, a, t, or g
<220> FEATURE:
<221> NAME/KEY: misc_feature
<222> LOCATION: (15)..(15)
<223> OTHER INFORMATION: n is a, c, t, or g
<220> FEATURE:
<221> NAME/KEY: misc_feature
<222> LOCATION: (16)..(16)
<223> OTHER INFORMATION: n is g, a, t, or c
<220> FEATURE:
<221> NAME/KEY: misc_feature
<222> LOCATION: (17)..(17)
<223> OTHER INFORMATION: n is g, a, or t
<220> FEATURE:
<221> NAME/KEY: misc_feature
<222> LOCATION: (18)..(18)
<223> OTHER INFORMATION: n is c, t, or a
<220> FEATURE:
<221> NAME/KEY: misc_feature
<222> LOCATION: (19)..(19)
<223> OTHER INFORMATION: n is g, t, or a
<220> FEATURE:
<221> NAME/KEY: misc_feature
<222> LOCATION: (20)..(20)
<223> OTHER INFORMATION: n is g, a, or t
<220> FEATURE:
<221> NAME/KEY: misc_feature
<222> LOCATION: (21)..(21)
<223> OTHER INFORMATION: n is g, c, t, or a
<220> FEATURE:
<221> NAME/KEY: misc_feature
<222> LOCATION: (22)..(22)
<223> OTHER INFORMATION: n is g, t, a, or c
<220> FEATURE:
<221> NAME/KEY: misc_feature
<222> LOCATION: (23)..(23)
<223> OTHER INFORMATION: n is g, t, or c
<220> FEATURE:
<221> NAME/KEY: misc_feature
<222> LOCATION: (24)..(24)
<223> OTHER INFORMATION: n is t, c, or g
<220> FEATURE:
<221> NAME/KEY: misc_feature
```

```
<222> LOCATION: (25)..(25)
<223> OTHER INFORMATION: n is t, g, a, or c
<220> FEATURE:
<221> NAME/KEY: misc_feature
<222> LOCATION: (26)..(26)
<223> OTHER INFORMATION: n is a, g, or c
<220> FEATURE:
<221> NAME/KEY: misc_feature
<222> LOCATION: (27)..(27)
<223> OTHER INFORMATION: n is g, c, t, or a
<220> FEATURE:
<221> NAME/KEY: misc_feature
<222> LOCATION: (28)..(28)
<223> OTHER INFORMATION: n is g, a, t, or c
<220> FEATURE:
<221> NAME/KEY: misc_feature
<222> LOCATION: (29)..(29)
<223> OTHER INFORMATION: n is g, t, or c
<220> FEATURE:
<221> NAME/KEY: misc_feature
<222> LOCATION: (30)..(30)
<223> OTHER INFORMATION: n is g, t, or a

<400> SEQUENCE: 26
nnnnnnnnnn nnnnnnnnnn nnnnnnnnnn                                    30
```

APTAMERS THAT BIND TO NATURAL AND SYNTHETIC CANNABINOIDS

GOVERNMENT SUPPORT

This invention was made with government support under Grant No. 2015-R2-CX-0034 awarded by the National Institute of Justice and under Grant No. DA045334 awarded by the National Institutes of Health. The government has certain rights in the invention.

SEQUENCE LISTING

The Sequence Listing for this application is labeled "SeqList-03Jun20-ST25.txt," which was created on Jun. 3, 2020, and is 8 KB. The Sequence Listing is incorporated herein by reference in its entirety.

BACKGROUND OF THE INVENTION

Bioreceptors are biological macromolecules that are defined by their ability to bind specific ligands. Many bioreceptors have been developed for molecular sensing in a variety of analytical contexts and for therapeutic purposes. Antibodies are the most widely used class of bioreceptors for sensing purposes. Antibodies are typically used both in the scientific community and commercially. Nevertheless, the shortcomings associated with antibodies have fueled interest in alternative reagents.

Aptamers are single-stranded oligonucleotides or peptides that are isolated from randomized nucleic-acid or peptide libraries through an in vitro method termed systematic evolution of ligands by exponential enrichment (SELEX). They have several characteristics that make them favorable as bioreceptors including high chemical stability, ease and affordability of synthesis, and low batch-to-batch variability alongside having high target-binding affinities and well-defined specificity. They have recently gained wide appeal as bioreceptors for biosensing, imaging, and therapeutics due to their low cost of production, ease of modification, chemical stability, and long shelf life. Nevertheless, the isolation of high-affinity oligonucleotide aptamers binding to small molecules is challenging especially when the target is hydrophobic and has limited functional groups for interaction with nucleic acids.

Extensive research has been performed on aptamers regarding their application in remedying a variety of problems in various areas such as medical diagnostics, environmental monitoring, drug detection, and food safety. In tandem, and arguably to a lesser extent, these applied research thrusts are supplemented by fundamental studies of aptamers, which primarily focus on the process by which they are generated (via SELEX) and the exact nature of the interaction of aptamers with their target ligands.

One fundamental and controversial question which has yet to be addressed is: Are there any ligands for which aptamers cannot be isolated? This boundary is well-defined for antibodies; limitations are related to the size of the target as well as its structure and physicochemical properties. There are certain molecules that lack immunogenicity, such as aliphatic or highly hydrophilic compounds such as glucose. Additionally, the antibody generation process is an in vivo process that disallows any precise control over the affinity and specificity of the resulting antibodies. It has been proffered that the in vitro nature of aptamer generation permits the development of bioreceptors for ligands that antibodies cannot be made for with precise control over affinity and specificity. In fact, aptamers have been isolated against targets as small as ions to as large as whole cells, achievements that are unreported for antibodies.

Nevertheless, several accounts suggest that there are certain molecules, to which it is challenging for aptamers to bind. It has been reported that the success rate of SELEX experiments with native DNA libraries is no greater than 30%. Several attempts were made to incorporate new chemistries into nucleic acid libraries to develop aptamers with augmented binding characteristics. Initial success was made by isolating aptamers from libraries containing a single modified nucleotide. Later works developed novel systems that enabled the incorporation of multiple non-canonical moieties in nucleic acid libraries, such as LOOPER and Aegis, to adopt a diverse array of amino-acid-like residues in both DNA and RNA. Although the benefit of using modified libraries in aptamer isolation have been demonstrated in numerous works, SELEX with modified libraries requires additional steps, specifically-engineered polymerases to incorporate modified bases, and/or specialized sequencing methods to identify the sequence of aptamers, all of which increases the cost and reduces the efficiency of SELEX. Meanwhile, aptamers containing custom modified bases may not be commercially accessible. In addition, studies with modified libraries are only limited to proteinaceous targets, and there are no such insights into the limitations that aptamers have with respect to small molecules.

Small-molecule targets are thought to be more difficult to isolate aptamers for, given that they have fewer sites for interaction and binding than macromolecules. It is generally believed, for example, that it is difficult to obtain aptamers for hydrophobic (e.g., cannabinoids such as tetrahydrocannabinol (THC)) and anionic compounds. Attempts have been made using modified libraries with artificial bases; however, these methods are laborious, expensive, and require specially-engineered biomaterials.

Thus, there is a need to develop methods to isolate aptamers that can bind challenging small molecules, e.g., hydrophobic and anionic compounds, and use such aptamers for rapidly and selectively detecting these small molecules.

BRIEF SUMMARY OF THE INVENTION

The subject invention provides methods, assays, and materials for rapid and specific detection of small molecules in a sample, in particular, in both clinical and field settings. In one embodiment, the method for detecting a small-molecule target in a sample comprises contacting the sample with an aptamer-based sensor selective for the small-molecule target, and detecting the small-molecule target in the sample. Advantageously, the aptamer-based sensor comprises one or more aptamers having low nanomolar affinity for their targets and minimal response to structurally-similar compounds.

In one embodiment, the detection of the small-molecule target comprises measuring a signal generated upon assembly of the aptamer-target complex. In another embodiment, the method further comprises determining the concentration of the small-molecule target in the sample.

In one embodiment, the subject invention provides methods for isolating aptamers that specifically bind to small molecules that are challenging for nucleic acids to bind. The success in generating aptamers, according to the subject invention, for these challenging small molecules shows the great impact that the selection conditions can have on the outcome of SELEX experiments. Such results greatly improve confidence in the capability of natural nucleic acid libraries to be used for selection experiments and underscores the hazard in assigning the failure of in vitro selection experiments to the structural and chemical limitations of natural nucleic acids.

In one embodiment, the small molecules according to the subject invention are drug molecules, including cannabinoids such as natural cannabinoids, synthetic cannabinoids, cannabinoid derivative and cannabimimetics. Cannabinoids are chemical compounds that bind to cannabinoid receptors in a subject.

In one embodiment, the natural cannabinoids are tetrahydrocannabinols (THC), including delta-8-tetrahydrocannabinol (Δ8-THC), delta-9-tetrahydrocannabinol (Δ9-THC), and/or THC metabolites (e.g., THC-COOH). The synthetic cannabinoids are, for example, selected from XLR-11 and UR-144.

In one embodiment, the aptamer-based sensor comprises one or more aptamers according to the subject invention and, optionally, a complementary nucleic acid sequence. In a further embodiment, the aptamer-based sensor comprises an aptamer, the aptamer comprising a nucleic acid sequence selected from SEQ ID Nos: 9-25. The complementary nucleic acid sequence may comprise a sequence of SEQ ID No: 8.

In one embodiment, the aptamer comprises a nucleic acid sequence selected from SEQ ID Nos: 9-25 and sequences sharing at least 50%, 55%, 60%, 65%, 70%, 75%, 80%, 85%, 90%, 95% or 99% identity with SEQ ID Nos: 9-25. In a further embodiment, the aptamer comprises a sequence of SEQ ID No: 3, 4, 5, 6, 7 or sequences sharing at least 50%, 55%, 60%, 65%, 70%, 75%, 80%, 85%, 90%, 95% or 99% identity with SEQ ID Nos: 3-7. In specific embodiments, the aptamer comprises a nucleic acid sequence selected from SEQ ID Nos: 3-7.

In one embodiment, the method according to the subject invention comprises contacting the sample with a aptamer-based sensor selective for a small-molecule target, wherein the aptamer-based sensor comprises an aptamer that specifically binds to the small-molecule target, and detecting the small-molecule target in the sample, wherein the detection of the small-molecule target comprises measuring a signal generated upon binding of the small-molecule targets to the binding domain of the aptamer.

In one embodiment, the method for rapid, sensitive and specific detection of natural cannabinoids in a sample comprises contacting the sample with a aptamer-based sensor selective for natural cannabinoids, wherein the aptamer-based sensor comprises a aptamer that binds to natural cannabinoids and, optionally, a complementary nucleic acid sequence, and detecting whether a signal change occurs, the signal change being indicative of the presence of the natural cannabinoids in the sample.

In one embodiment, the method for rapid, sensitive and specific detection of synthetic cannabinoids in a sample comprises contacting the sample with a aptamer-based sensor selective for synthetic cannabinoids, wherein the aptamer-based sensor comprises a aptamer that binds to synthetic cannabinoids and, optionally, a complementary nucleic acid sequence, and detecting whether a signal change occurs, the signal change being indicative of the presence of the natural cannabinoids in the sample.

BRIEF DESCRIPTION OF THE DRAWINGS

FIGS. 4A-4D show aptamer sequence identification from the final pool and characterization of the target-binding affinity of THC-binding aptamer termed THC1.2. (A) Sequence logo for the 45 clones obtained from the round 11 pool showing the nucleotide diversity at each position of the random domain (SEQ ID NO: 26). A larger font-size represents higher frequency. (B) Schematic of a previously reported strand-displacement fluorescence assay for determining the target-binding affinity of THC1.2. (C) Binding affinity between an Iowa Black RQ-labeled complementary DNA strand (Q-cDNA) and Cy5-labeled aptamer (F-THC1.2) ($K_{D1}$) determined by titrating different concentrations of Q-cDNA into 40 nM of F-THC1.2 and measuring fluorescence quenching at 668 nm. The x-axis indicates the free concentration of Q-cDNA. (D) Binding affinity between THC and the F-THC1.2-Q-cDNA complex ($K_{D2}$) determined from fluorescence recovery at 668 nm of 40 nM of F-THC1.2 mixed with 125 nM Q-cDNA in the absence and presence of varying concentrations of THC. Error bar represents standard deviations for three experiments.

FIG. 5 shows the secondary structure of THC1.2 (SEQ ID No: 3) and free energy of structure as predicted by Mfold.

FIG. 6 shows $K_D$ of THC-COOH for THC1.2 based on the strand-displacement fluorescence assay.

FIGS. 7A-7B show the characterization of the target-binding affinity of THC1.2 using isothermal titration calorimetry (ITC). Top panels present raw data showing the heat generated from each titration of (A) THC or (B) THC-COOH to THC1.2, while bottom panels show the integrated heat of each titration after correcting for dilution heat of the titrant. ITC data were fitted using a single-site model.

FIGS. 11A-11B show the characterization of the combined round 4.2 pool after four rounds of parallel selection. The (A) XLR-11-binding affinity and (B) cross-reactivity of the combined round 4.2 pool determined using the gel elution assay. (Abbreviation: ABZ=albendazole, TCP=tocopherol, 5-HT=serotonin, Trp=tryptophan, a-PVP=α-pyrrolidinovalerophenone, GNS=granisetron, NIC=nicotine, CAF=caffeine, MET=methamphetamine, COC=cocaine).

FIGS. 12A-12F show the characterization of pool affinity and specificity using a gel elution assay. XLR-11-binding affinity and cross-reactivity to UR-144 and counter-targets for the (A and B) round 8.2 pool, (C and D) round 8.3 pool, and (E and F) round 17.3 pool. (Abbreviation: ABZ=albendazole, TCP=tocopherol, 5-HT=serotonin, Trp=tryptophan, a-PVP=α-pyrrolidinovalerophenone, GNS=granisetron, NIC=nicotine, CAF=caffeine, MET=methamphetamine, COC=cocaine).

FIGS. 13A-13D show the selection progress of the SELEX for isolating an XLR-11/UR-144-binding aptamer. (A) Percent XLR-11-induced pool elution, (B) XLR-11-binding affinity, (C) UR-144 and (D) THC cross-reactivity of the round 4, 6, 8, 10, 12, 14, and 17 pools as determined using a gel elution assay.

FIGS. 14A-14E show the identification of aptamer sequences (XA1 and XA2) and characterization of their target-binding affinity. (A) Population of sequences in the XA1 family (purple dots), XA2 family (yellow dots), and other sequences (gray dots) in the pools after Round 16 and Round 17 obtained from high-throughput sequencing. (B) Secondary structure of XA1 (SEQ ID NO: 4) and XA2 (SEQ ID NO: 5) and their free energy as predicted by Mfold. (C) The sequences of random domains (SEQ ID NOs: 24 and 25), pool population, and target-binding affinity (according to ITC) of XA1 and XA2, respectively. (D and E) Characterization of target-binding affinity of XA1 using the strand-displacement fluorescence assay.

FIGS. 15A-15D show the target-binding affinity of XA1 and XA2 characterized by ITC. Titration of (A) XLR-11 to XA1, (B) UR-144 to XA1, (C) XLR-11 to XA2, (D) UR-144 to XA2. The detailed conditions are listed in Table S2. ITC data were fitted using a single-site model.

FIGS. 18A-18C show dye-displacement assay for colorimetric detection of THC. (A) Spectra of ETC at various concentration of THC (0, 0.25, 0.5, 1, 1.5, 2, 2.5, 3.5, 5, 10 and 20 µM) and (B) the corresponding calibration curve. Inset shows the assay response at low concentrations of the target. (C) Cross-reactivity of THC, THC-COOH, CBN and THCA at a concentration of 5 CBD, CBDA, CBG, CBGA, UR-144 and XLR-11 at a concentration of 25 µM and other small molecule drugs at a concentration of 100 µM. Cross-reactivity was calculated relative to the signal gain produced by 5 µM THC. Inset represents the photographic image of the assay for the specificity test. Error bars represent the standard deviation of measurements with three individual experiments. Abbreviation: Meth=methamphetamine.

BRIEF DESCRIPTION OF SEQUENCES

Figure 1:
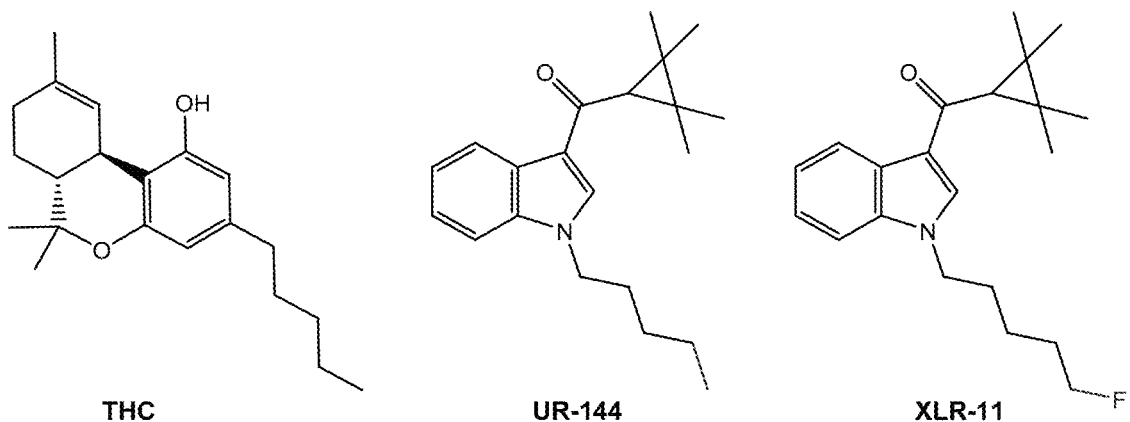
FIG. 1 shows the chemical structure of THC, UR-144 and XLR-11.

SEQ ID NO: 1 is a cDNA sequence contemplated for use according to the subject invention.

SEQ ID NO: 2 is a DNA library contemplated for use according to the subject invention, wherein N are random bases.

SEQ ID NO: 3 is a sequence of a DNA aptamer contemplated for use according to the subject invention.

SEQ ID NO: 4 is a sequence of a DNA aptamer contemplated for use according to the subject invention.

SEQ ID NO: 5 is a sequence of a DNA aptamer contemplated for use according to the subject invention.

SEQ ID NO: 6 is a sequence of a DNA aptamer with fluorescent label contemplated for use according to the subject invention.

SEQ ID NO: 7 is a sequence of a DNA aptamer with fluorescent label contemplated for use according to the subject invention.

SEQ ID NO: 8 is a quencher-modified cDNA complementary strand for use according to the subject invention.

SEQ ID NOs: 9-26 are sequences of random regions of aptamers contemplated for use according to the subject invention.

DETAILED DESCRIPTION OF THE INVENTION

The subject invention provides methods, assays and materials for rapid and specific detection of small molecules in a sample, in particular, in both clinical and field settings. In one embodiment, the method for detecting a small-molecule target in a sample comprises contacting the sample with an aptamer-based sensor selective for the small-molecule target, and detecting the small-molecule target in the sample. Advantageously, the aptamer-based sensor comprises one or more aptamers, according to the subjection, having low nanomolar affinity for their targets and minimal response to structurally-similar compounds.

In one embodiment, the detection of the small-molecule target comprises measuring a signal generated upon assembly of the aptamer-target complex. In another embodiment, the method further comprises determining the concentration of the small-molecule target in the sample.

In one embodiment, the sample is a biological sample of a subject. In specific embodiments, the biological sample is selected from blood, plasma, urine, tears, sweat, and saliva. The subject may be any animal or human, preferably, a human. The subject may also be any animal including, but not limited to, non-human primates, rodents, dogs, cats, horses, cattle, pigs, sheep, goats, chickens, guinea pigs, hamsters and the like.

In one embodiment, the sample is an environmental sample, for example, water, soil, air, or plant sample. In another embodiment, the sample is a seized sample, e.g., seized drug sample, for instance, a plant material sample, or a street drug sample seized by law enforcement or school or government officials.

The subject invention provides methods for isolating nucleic acid molecules, e.g., aptamers, which bind to "challenging" small molecules with high target-affinity and specificity. Advantageously, the methods of the subject invention use appropriate selection strategy and conditions, and include next generation sequencing techniques and bioinformatics.

The subjection invention provides functional nucleic acids that bind to "challenging" small molecules with high target-affinity and specificity. Such functional nucleic acids, e.g., aptamers, can be directly isolated from unmodified DNA libraries through SELEX by e.g., library-immobilized SELEX method.

Small Molecules

The term "small molecule" or "small-molecule target" used herein extends to any molecule capable of being detected using an aptamer technique. In specific embodiments, the small-molecule target may be an amino acid, an amino acid-related molecule, a peptide, a steroid, a lipid, a sugar, a carbohydrate, a biomarker, a drug molecule, a drug metabolite, a coenzyme, a nucleotide (nt), a nucleotide-related molecule, a pyridine nucleotide, a cyclic nucleotide, or a cyclic dinucleotide. In another embodiment, the small-molecule target may be an infective agent, antigen, toxin, disease biomarker and/or specific metal ion.

The "challenging" small molecules refer to small molecules that are typically hydrophobic and have a limited number of epitopes for forming strong interaction with nucleic acids. These small molecules, in general, have low water-solubility.

In one embodiment, the "challenging" small molecules according to the subject invention are drug molecules, including cannabinoids such as natural cannabinoids, synthetic cannabinoids, cannabinoid derivatives and cannabimimetics. Cannabinoids are chemical compounds that bind to cannabinoid receptors in a subject. Cannabinoids are produced in animals, plants, and synthetically. Over 100 cannabinoids have been identified. Natural cannabinoids include endocannabinoids that are produced naturally in the body of animals, and phytocannabinoids that are produced naturally in plants such as *Cannabis* plants. Synthetic cannabinoids are manufactured artificially.

The term "*Cannabis* plant(s)" includes wild-type *Cannabis sativa* and variants thereof, including *Cannabis* chemovars, which naturally contain different amounts of the individual cannabinoids and also plants that are the result of genetic crosses, self-crosses, or hybrids thereof.

Phytocannabinoids include, but are not limited to, tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE), and cannabicitran (CBT).

Endocannabinoids include, but are not limited to, arachidonoylethanolamine (Anandamide or AEA), 2-arachidonoylglycerol (2-AG), 2-arachidonyl glyceryl ether, N-arachidonoyl dopamine (NADA), virodhamine (OAE), and lysophosphatidylinositol (LPI).

Synthetic cannabinoids are agonists of the cannabinoid receptors. They have been designed to be similar to THC. The synthetic analogs often have greater binding affinity and greater potency to the cannabinoid receptors. There are several synthetic cannabinoid families (e.g. CP-, WIN-, JWH-, UR- and PB-) classified based on the base structure. Synthetic cannabinoids include, but are not limited to naphthoylindoles (e.g., JWH-007 and JWH-018), naphthylmethylindoles (e.g., JWH-073 and JWH-200), naphthoylpyrroles (e.g., JWH-398, and AM-1221), naphthylmethylindenes (e.g., AM-2201, AM-694, and WIN-55,212-2), phenylacetylindoles (e.g., JWH-250, and RCS-8), cyclohexylphenols (e.g., CP-47,947, and CP-55,940), tetramethylcyclopropylindoles (e.g., UR-144 and XLR-11), adamantoylindoles (e.g., 5F-AKB-48, APICA, and STS-135), indazole carboxamides (e.g., AB-PINACA, and AB-FUBINACA), and quinolinyl ester (e.g., PB-22, and 5F-PB-22).

The cannabimimetics refer to compounds that are ligands of cannabinoid receptors, but may not be structurally related to classical cannabinoids such as THC. Such cannabimimetics include, but are not limited to, the aminoalkylindoles, 1, 5-diarylpyrazoles, quinolines, and arylsulfonamides. Other cannabinoids may also include, for example, pharmaceutically acceptable salts of cannabinoids.

In a specific embodiment, the cannabinoid is THC, including delta-8-tetrahydrocannabinol (Δ8-THC), delta-9-tetrahydrocannabinol (Δ9-THC), THC metabolites (e.g., THC-COOH), and/or THC-conjugated molecules. THC is the primary psychoactive component of the *Cannabis* plant. It has very low water solubility, no charge, and very few functional groups capable of forming strong interactions with nucleic acids.

In one embodiment, the small molecules are cannabinoids having structures comprising one or more functional groups selected from phenol, ether, benzene, alkene, alkyl, indole ring, ketone, pentyl tail, and tetramethylcyclopropyl ring. Preferably, the cannabinoid has a structure comprising one or more functional groups selected from alkyl, phenol, ether, benzene, and alkene. Alternatively, the cannabinoid has a structure comprising one or more functional groups selected from alkyl, indole ring, ketone, pentyl tail, and tetramethylcyclopropyl ring.

In a specific embodiment, the cannabinoid is selected from THC, metabolites thereof, cannabinol (CBN), tetrahydrocannabivarin (THCV), XLR-11 and UR-144.

Aptamers

The subject invention provides aptamer-based sensors for use in detecting natural and synthetic cannabinoids. The aptamers of the subject invention are nucleic acid molecules characterized by the ability to bind to a target molecule with high specificity and high affinity. Almost every aptamer identified to date is a non-naturally occurring molecule. Aptamers to a given target may be identified and/or produced by the method of systematic evolution of ligands by exponential enrichment (SELEX).

In one embodiment, the aptamer-based sensor comprises one or more aptamers according to the subject invention and, optionally, one or more complementary nucleic acid sequences. In specific embodiments, the aptamer-based sensor comprises an aptamer, the aptamer comprising a nucleic acid sequence selected from SEQ ID Nos: 9-25. The complementary nucleic acid sequence may comprise a sequence of SEQ ID No: 8.

The aptamers are identified using the library-immobilized SELEX method where the library is immobilized on a solid support. Preferably, the library is a DNA library comprising at least $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $6\times10^{14}$ oligonucleotides. The DNA library comprises more than one library pool. The same or different library pools may be used for each of the natural and/or synthetic cannabinoids in the family.

As used herein, the terms "library," "nucleic acid library," "polynucleotide library," and the like, generally refer to a mixture of nucleic acid molecules having variable sequences from which an aptamer is selected for a specific target or target family of small molecules. The nucleic acid molecules of the library have a length ranging from about 5 to about 500 nucleotides, to about 450 nucleotides, to about 400 nucleotides, to about 350 nucleotides, to about 300 nucleotides, to about 250 nucleotides, to about 200 nucleotides, to about 150 nucleotides, to about 100 nucleotides, or to about 50 nucleotides. In some embodiments, the nucleic acid molecules of the library have a length between about 10 nucleotides and about 100 nucleotides, between about 20 nucleotides and about 90 nucleotides, between about 30 nucleotides and about 70 nucleotides, or between about 40 nucleotides and about 60 nucleotides. In certain embodiments, the nucleic acid molecules of the library have a length of 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides.

The constituent molecules of a nucleic acid library may be naturally occurring nucleic acids or fragments thereof (e.g., in a cDNA or EST library), chemically synthesized nucleic acids, enzymatically synthesized nucleic acids or nucleic acids made using any combination of the aforementioned techniques. Preferably, the nucleic acid library comprises sequences of unmodified nucleic acids.

In some embodiments, each nucleic acid molecule in the library may include one or more fixed (e.g., known) nucleotide sequences 5' to, 3' to, or flanking, the variable region for the purpose of facilitating the enrichment and identification of target aptamers (such as by using PCR, affinity chromatography, or any similar methods used to purify or enrich target nucleic acids).

In a specific embodiment, each library strand comprises a stem-loop structure and 73 nucleotides in length. Such library strand comprises a stem having at least 4, 5, 6, 7, 8, or 9 base-pairs and a randomized loop region comprising 25, 26, 27, 28, 29, 30, 31, 32 or 33 nucleotides.

In a preferred embodiment, the DNA library comprises a sequence of SEQ ID NO: 2 where N represents a random nucleotide and N30 represents the randomized 30 nucleotides. The randomized nucleotides are each independently selected from adenine (A), thymine (T), cytosine (C) and guanine (G). The randomized region comprises the target-binding domain of the aptamer. Preferably, the randomized region is the target-binding domain of the aptamer. In a specific embodiment, the randomized region comprises a sequence selected from SEQ ID Nos: 9-26.

The aptamers isolated according to the subject invention are capable of binding to the small molecule of interest, such as natural and/or synthetic cannabinoids. The aptamer is an oligonucleotide, such as DNA or RNA molecules and may be single-stranded. In a preferred embodiment, the aptamer is a DNA aptamer.

As used herein, the terms "polynucleotide," "nucleotide," "oligonucleotide," and "nucleic acid" can be used to refer to a nucleic acid comprising DNA, RNA, derivatives thereof, or combinations thereof.

The aptamer may be partially or fully folded to form various secondary structures (e.g., stems, loops, bulges, pseudoknots, G-quadruplexes and kissing hairpins), which in turn can form unique three-dimensional architectures able to specifically recognize their targets by exploiting a variety of interactions such as hydrophobic and electrostatic interactions, hydrogen bonding, van der Waals forces, and π-π stacking as well as shape complementarity.

In certain embodiments, the aptamer according to the present invention may comprise at least 20, at least 30, at least 40, at least 50, at least 60, at least 70, or at least 80 nucleotides. The aptamer, preferably, comprises 20 to 200 nucleotides, preferably 25 to 150 nucleotides, more preferably 30 to 100 nucleotides, most preferably, 35 to 60 nucleotides.

In one embodiment, the aptamer according to the present invention may have a minimum length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. The aptamer according to the present invention may have a maximum length of, for example, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 nucleotides. The aptamer according to the present invention may have a length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In some embodiments, the aptamers according to the subject invention may have free ends. For example, the 3' and 5' ends may not be ligated to form a loop, although they may be conjugated to other molecules or otherwise modified. The aptamers may adopt a tertiary structure such as a hairpin loop. In some embodiments, the aptamers may be looped. For example, the 5' and 3' ends of the nucleic acid are covalently bonded to form a loop not having any free ends.

In one embodiment, the aptamer according to the subject invention comprises at least one stems, two stems, or three stems. Each stem may be fully or partially complementary. Each stem may comprise the same or different number of nucleotides. Exemplary lengths of each stem may be 1, 2, 3, 4, 5, 6, 7, 8, 9, 10, 11, 12, 13, 14, or 15 base pairs. Other exemplary lengths of each stem may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. A partially complementary stem may comprise more than one wobble base pair.

In one embodiment, the aptamer comprises at least one junction, which is formed when two or more stems meet. In certain embodiments, the junction may be a loop between two stems, or a three-way junction (TWJ). The junction may comprise, for example, 10, 11, 12, 13, 14, 15, 16, 17, 18, 19, 20, 21, 22, 23, 24, 25, 26, 27, 28, 29, or 30 nucleotides. The junction in an aptamer can serve as a binding domain for a small-molecule target.

In one embodiment, the aptamer has at least one hairpin/stem-loop structure. The loop may have a minimum length of, for example, 10, 11, 12, 13, 14, 15, 16, 17, 18, 19, 20, 21, 22, 23, 24, 25, 26, 27, 28, 29, or 30 nucleotides. The loop may have a maximum length of, for example, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides. The loop may comprise, for example, 20, 21, 22, 23, 24, 25, 26, 27, 28, 29, 30, 31, 32, 33, 34, 35, 36, 37, 38, 39, or 40 nucleotides. Preferably, the loop comprises 30 nucleotides. The loop region is the target-binding site of the aptamer. In specific embodiments, the aptamer comprises a stem and a loop region, the loop region comprising a sequence selected from SEQ ID NOs: 9-25. The loop region is specific for binding small molecules of interest.

In one embodiment, the aptamer comprises a nucleic acid sequence selected from SEQ ID Nos: 9-25 and sequences sharing at least 50%, 55%, 60%, 65%, 70%, 75%, 80%, 85%, 90%, 95% or 99% identity with SEQ ID Nos: 9-25. In another embodiment, the aptamer comprises SEQ ID No: 2 wherein the sequence of N30 is selected from SEQ ID Nos: 9-25. In a further embodiment, the aptamer comprises a sequence of SEQ ID No: 3, 4, 5, 6, 7 or sequences sharing at least 50%, 55%, 60%, 65%, 70%, 75%, 80%, 85%, 90%, 95% or 99% identity with SEQ ID Nos: 3-7. In specific embodiment, the aptamer comprises a nucleic acid sequence selected from SEQ ID Nos: 3-7. In a further embodiment, the aptamer consists of SEQ ID No: 3, 4, 5, 6 or 7.

In one embodiment, the aptamer comprises two or more copies of the nucleic acid sequence selected from SEQ ID Nos: 9-25 and/or sequences sharing at least 50%, 55%, 60%, 65%, 70%, 75%, 80%, 85%, 90%, 95% or 99% identity with SEQ ID Nos: 9-25. In another embodiment, the aptamer comprises SEQ ID No: 2 wherein the sequence of N30 is selected from SEQ ID Nos: 9-25. In a further embodiment, the aptamer comprises two or more copies of SEQ ID No: 3, 4, 5, 6, 7 and/or sequences sharing at least 50%, 55%, 60%, 65%, 70%, 75%, 80%, 85%, 90%, 95% or 99% identity with SEQ ID Nos: 3-7. In specific embodiment, the aptamer comprises two or more copies of the nucleic acid sequence selected from SEQ ID Nos: 3-7. In a further embodiment, the aptamer consists of two or more copies of SEQ ID No: 3, 4, 5, 6 or 7.

In one embodiment, the aptamer is rich in G. For example, the aptamer comprises at least 10, 11, 12, 13, 14, 15, 16, 17, 18, 19, 20, 21, 22, 23, 24 or 25 Gs. The target-binding domain of the aptamer may comprise at least 5, 6, 7, 8, 9, 10, 11, 12, 13, 14, 15, 16, 17, 18, 19, or 20 Gs. In specific embodiments, the aptamer comprises 10, 11, 12, 13, 14, 15, 16, 17, 18, 19, 20, 21, 22, 23, 24 or 25 Gs. The target-binding domain of the aptamer comprises 5, 6, 7, 8, 9, 10, 11, 12, 13, 14, 15, 16, 17, 18, 19, or 20 Gs.

The aptamer of the present invention may or may not be truncated after isolation. The truncation may occur from 5', 3' or both ends, up to 1, 2, 3, 4, 5, 6, 7, 8, 9, 10, 11, 12, 13, 14, 15, 16, 17, 18, 19 or 20 nucleotides.

The aptamers of the present invention may or may not include chemical modifications. The chemical modifications include a chemical substitution at a sugar position, a phosphate position, and/or a base position of the nucleic acid including, for example, incorporation of a modified nucleotide, incorporation of a capping moiety (e.g., 5' or 3' capping) or a tail moiety, conjugation to a high molecular weight, non-immunogenic compound (e.g., polyethylene glycol (PEG)), conjugation to a lipophilic compound, and substitutions in the phosphate backbone. Base modifications may include 5-position pyrimidine modifications, modifications at exocyclic amines, substitution of 4-thiouridine, substitution of 5-bromo- or 5-iodo-uracil, and backbone modifications. Sugar modifications may include 2'-amine nucleotides (2'-NH$_2$). 2'-fluoronucleotides (2'-F), and 2'-O-methyl (2'-OMe) nucleotides. Such modifications may improve the stability of the aptamers or make the aptamers more resistant to degradation. In some embodiments, each base of a given type (e.g., A, T, C, and G) may contain the same chemical modification.

In specific embodiments, the aptamer according to the subject invention may be modified by addition, subtraction, and substitution of one or more nucleotides from 5', 3' or both ends or within sequences of the stem region of the aptamer. Advantageously, such addition, subtraction and substitution of one or more nucleotides from 5', 3' or both ends of the aptamer may not affect the binding of the aptamer to small molecule targets. Such addition, subtraction and substitution of one or more nucleotides from 5', 3' or both ends of the aptamer are well established in the art.

The aptamers may or may not be modified by addition of one or more reporter labels (or detectable labels). In some embodiments, the label may be attached to either the 5' or 3' end of the aptamer. The label may also be attached with the backbone of the aptamer. The skilled person will be aware of techniques for attaching labels to nucleic acid strands. The detectable label may be attached directly or indirectly to the nucleic acid aptamer. If the label is indirectly attached to the nucleic acid aptamer, it may be by any mechanism known to one of skill in the art, such as using biotin and streptavidin.

The aptamers may or may not comprise a reporter label, such as a fluorescent dye, electroactive tag, nanoparticle (e.g., a gold nanoparticle (AuNP)), a fluorescent dye and quencher pair or an enzyme. Exemplary labels include, but are not limited to, an organic donor fluorophore or an organic acceptor fluorophore, a luminescent lanthanide, a fluorescent or luminescent nanoparticle, an affinity tag such as biotin, or a polypeptide. In some embodiments, the aptamer may comprise a fluorescent label, for example, fluorescein, TAMRA, rhodamine, Texas Red, Alexa Fluor (e.g., AlexaFluor 488, AlexaFluor 532, AlexaFluor 546, AlexaFluor 594, AlexaFluor 633 and AlexaFluor 647), cyanine dye (e.g., Cy7, Cy7.5, Cy5, Cy5.5 and Cy3), Tye dye (e.g., TYE 563, TYE 665, TYE 705), atto dye (e.g., Atto 594 and Atto 633), Hexachlorofluorescein, FAM (6-carboxyfluroescein), BODIPY FL, OliGreen, 40,6-diamidino-2-phenylindol (DAPI), Hoechst 33,258, malachite green (MG), and FITC. The nanoparticle can be an upconversion nanoparticle. Electroactive tag can be a methylene blue or ferrocene molecule.

In some embodiments, the fluorophore is selected from the group consisting of fluorophores that emit a blue, green, near red or far red fluorescence. In specific embodiments, the aptamer is labeled with Cy3, Cy5 or Cy7. Preferably, the aptamer is a Cy5-labeled aptamer comprising SEQ ID No: 6.

In some embodiments, the aptamer may bind to a complementary sequence. The aptamer and the complementary sequence may be labeled by a fluorescent dye and quencher pair. In certain embodiments, a fluorophore is conjugated at one end of the aptamer and a quencher at one end of the complementary sequence. In the absence of its target, the complementary sequence binds to the aptamer, thereby positioning the fluorophore close to the quencher. Target binding to the aptamer displaces the complementary sequence, resulting in the separation of the fluorophore and the quencher. The resulting recovery of the fluorescence signal directly reflects the extent of the binding and can be used for detection and quantitative measurement of the target concentration.

The quenchers can be, for example, Dabcyl, DDQ-I, Eclipse, Iowa Black FQ, BHQ-1, QSY-7, BHQ-2, DDQ-II, Iowa Black RQ, QSY-21, or BHQ-3.

In some embodiments, the fluorophore is at a location of, for example, 1st, 2nd, 3rd, 4th, 5th, 6th, 7th, 8th, 9th, or 10th nucleotide from either 5' end or 3' end of the aptamer. The quencher is at a location of, for example, 1st, 2nd, 3rd, 4th, 5th, 6th, 7th, 8th, 9th, or 10th nucleotide from either 3' end or 5' end of the complementary sequence.

In preferred embodiments, the location of the fluorophore and quencher is such that the proximity of the fluorophore and quencher in a complementary sequence binding conformation provide maximal quenching and the fluorophore and quencher in a separated conformation provide maximal fluorescence of the fluorophore. For optimized detection of fluorescence changes that allows utilization of aptamers for target detection, it is desirable that the fluorescence in the quenched conformation is as low as possible and the fluorescence in the unquenched conformation is as high as possible combined with the most rapid interconversion from one conformation to the other.

In one embodiment, the aptamer can bind a dye such as a fluorophore with the target-binding domain. In one embodiment, the aptamer has inherent dye-displacement functionality. A dye can bind within the binding domain of the aptamer and the dye can be displaced in the presence of the small-molecule target, resulting in a change in absorbance. Such change may occur within seconds. Such change can also directly reflect the extent of target binding and be used for detection and quantitative measurement of the target concentration.

In specific embodiments, the aptamer specifically recognizes natural and synthetic cannabinoids, derivative and/or mimetics thereof. The aptamer can specifically bind to, for example, THC with nanomolar dissociation constant and does not bind to structurally-similar cannabinoids such as cannabidiol and cannabinol. In one embodiment, the aptamer also binds to the urinary metabolite of THC, THC-COOH.

In a specific embodiment, the aptamer can specifically bind to, for example, the synthetic cannabinoids UR-144 and XLR-11, each with nanomolar dissociation constant and does not bind to structurally-similar cannabinoids such as cannabidiol and cannabinol.

In one embodiment, the aptamer according to the subject invention is cross-reactive to THC-COOH cannabinol (CBN) and tetrahydrocannabivarin (THCV), but does not bind to other cannabinoids including tetrahydrocannabinolic acid (THCA), cannabigerolic acid (CBGA), cannabidiolic acid (CBDA), cannabigerol (CBG), and cannabidiol (CBD), at a concentration of 10 µM.

In specific embodiments, alteration of substituents at the aromatic ring or opening of the ether group of the structures of cannabinoids completely impairs aptamer recognition, which implies that these functional groups are involved in target binding. Shortening the alkyl tail results in a great reduction in target binding affinity, implying that the size and shape of the ligand plays a role in binding aptamer. Further, modification of the cyclohexene ring only moderately reduces binding affinity, indicating less involvement of these regions in aptamer binding.

In one embodiment, the aptamer, e.g., THC1.2 (SEQ ID No: 3) does not show cross-reactivity to other interferents including common illicit drugs (e.g., XLR-11, UR-144, cocaine, methamphetamine, amphetamine, methcathinone, α-PVP, and pentylone), pharmaceuticals (e.g., clonazepam, pseudoephedrine, acetaminophen, and ibuprofen), cutting agents (e.g., caffeine and procaine), and nicotine.

In one embodiment, the aptamer, e.g., XA1 (SEQ ID No: 4) and XA2 (SEQ ID No: 5) does not show cross-reactivity to other interferents including UR-144M, amphetamine (AMP), methcathinone (MCA), pentylone (PTL), clonazepam (CLZ), pseudoephedrine ((+)-PSE), procaine (PRC), acetaminophen (ACM), ibuprofen (IBU), albendazole (ABZ), tocopherol (TCP). Serotonin (5-HT), tryptophan (Trp), α-pyrrolidinovalerophenone (α-PVP), nicotine (NIC), caffeine (CAF), methamphetamine (MET), granisetron (GNS) and cocaine (COC).

In one embodiment, the aptamer binds to the small molecule with a dissociation constant of, for example, about 10 nM, about 50 nM, about 100 nM, about 150 nM, about 200 nM, about 250 nM, about 300 nM, about 350 nM, about 400 nM, about 450 nM, about 500 nM, about 550 nM, about 600 nM, about 650 nM, about 700 nM, about 750 nM, about 800 nM, about 850 nM, about 900 nM, about 950 nM, about 1 µM, about 2 µM, about 3 µM, about 4 µM, about 5 µlA about 6 µM, about 7 µM, about 8 µM, about 9 µM, or about 10 µM.

Method of Using the Aptamer

The aptamers according to the subject invention have high binding affinity and specificity for their targets, which enables their use for sensitive detection of cannabinoids for analytical purposes.

The subject invention provides aptamer-based sensors for rapid, sensitive and specific detection of small-molecule targets in a sample. The aptamer-based sensor comprises an aptamer that binds to natural and/or synthetic cannabinoids. The subject invention also provides methods of using the aptamer-based sensor for detecting one or more small-molecule targets in a complex sample.

In one embodiment, the method for detecting a small-molecule target comprises contacting the sample with a aptamer-based sensor selective for a small-molecule target, wherein the aptamer-based sensor comprises an aptamer that specifically binds to the small-molecule target, and detecting the small-molecule target in the sample, wherein the detection of the small-molecule target comprises measuring a signal generated upon binding of the small-molecule targets to the binding domain of the aptamer.

In one embodiment, the aptamer-based sensor further comprises a nucleic acid sequence that is complementary to up to 8, 9, 10, 11, 12, 13, 14, or 15 nucleotides from the 5' or 3' end of the aptamer of the subject invention. The complementary nucleic acid sequence comprises at least 5, 6, 7, 8, 9, 10, 11, 12, 13, 14, or 15 nucleotides. Exemplary lengths of each stem may be 10, 11, 12, 13, 14, or 15 nucleotides.

In specific embodiments, the aptamer-based sensor is labeled with a fluorophore-quencher pair wherein the aptamer comprises a fluorophore at the 5' or 3' end while the complementary nucleic acid sequence comprises a quencher at the 3' or 5' end. In a preferred embodiment, the fluorophore is Cy5 and the quencher is a BHQ quencher.

In one embodiment, the method further comprises determining the concentration of the small-molecule target in the sample. The determination can comprise comparing the signal generated upon target binding with a standard curve of such signal. For example, the determination comprises comparing the absorbance signal generated upon binding of aptamer-target complex with a standard curve of the absorbance of Cy5. The absorbance read-out can be quantified in seconds by, for example, a microplate-reader or portable photometer, allowing for high-throughput or on-site detection, respectively.

In one embodiment, the aptamer is a natural cannabinoid-binding aptamer that specifically binds to natural cannabinoids, e.g., THC, metabolite and derivative thereof. The natural cannabinoid-binding aptamer comprises a nucleic acid sequence of SEQ ID NO: 9 or a sequence sharing at least 50%, 55%, 60%, 65%, 70%, 75%, 80%, 85%, 90%, 95%, 98%, or 99% identity with SEQ ID NO: 9. Preferably, the natural cannabinoid-binding aptamer comprises a nucleic acid sequence of SEQ ID NO: 3, 6 or a sequence sharing at least 50%, 55%, 60%, 65%, 70%, 75%, 80%, 85%, 90%, 95%, 98%, or 99% identity with SEQ ID NO: 3 or 6.

In another embodiment, the aptamer is a synthetic cannabinoid-binding aptamer that specifically binds to synthetic cannabinoids, e.g., XLR-11, UR-144 and derivatives thereof. Preferably, the synthetic cannabinoid-binding aptamer comprises a nucleic acid sequence selected from SEQ ID NOs: 24-25 and sequences sharing at least 50%, 55%, 60%, 65%, 70%, 75%, 80%, 85%, 90%, 95%, 98%, or 99% identity with SEQ ID NOs: 24-25. More preferably, the synthetic cannabinoid-binding aptamer comprises a nucleic acid sequence of SEQ ID NO: 4, 5, 7 or a sequence sharing at least 50%, 55%, 60%, 65%, 70%, 75%, 80%, 85%, 90%, 95%, 98%, or 99% identity with SEQ ID No: 4, 5 or 7.

In one embodiment; the method for rapid, sensitive and specific detection of natural cannabinoids in a sample comprises contacting the sample with a aptamer-based sensor selective for natural cannabinoids, wherein the aptamer-based sensor comprises a aptamer that binds to natural cannabinoids and, optionally, a complementary nucleic acid sequence or a dye, and detecting whether a signal change occurs, the signal being a change in color, absorbance or fluorescence intensity, the signal change being indicative of the presence of the natural cannabinoids in the sample.

In one embodiment, the method for rapid, sensitive and specific detection of synthetic cannabinoids in a sample comprises contacting the sample with a aptamer-based sensor selective for synthetic cannabinoids, wherein the aptamer-based sensor comprises a aptamer that binds to synthetic cannabinoids and, optionally, a complementary nucleic acid sequence or a dye, and detecting whether a signal change occurs, the signal being a change in color, absorbance or fluorescence intensity, the signal change being indicative of the presence of the synthetic cannabinoids in the sample.

In one embodiment, the subject invention provides an assay employing dye-displacement strategies for the detection of small-molecule targets. In such assay, a small-molecule dye is initially associated with the binding domain of an aptamer. The presence of the small-molecule target causes displacement of the dye from the binding domain, resulting in a change in the color, absorbance or fluorescence of the dye.

Advantageously, because the aptamers typically bind to these small-molecule targets and dyes with similar affinities, target-induced dye-displacement is more thermodynamically feasible than the displacement of a tightly-bound complementary strand. The aptamer used for such assay does not need to be labeled and can be label free. The dye-displacement assays can achieve a much lower detection limit.

In such assay, the dye molecule is initially associated with the binding domain of the cannabinoid-binding aptamer. The presence of cannabinoid causes the displacement of the dye molecule from the binding domain, resulting in a change in its color, absorbance or fluorescence.

Advantageously, the assay has excellent specificity because the aptamer does not cross-react to other interferents, for example, THCA, CBD, CBDA, CBG, CBGA, UR-144, XLR-11, cocaine, amphetamine, Heroin, α-PVP, methamphetamine, pentylone, procaine, acetaminophen, ibuprofen, nicotine, caffeine, clonazepam, and fentanyl. Also, in certain embodiments, the colorimetric dye-displacement assay detects nanomolar concentrations (e.g., as low as 250 nM) of natural and/or synthetic cannabinoids, even in, for example, urine and saliva in a label-free manner via instrumental means.

The subject invention provides aptamer-based sensors for rapid and naked-eye detection of natural and/or synthetic cannabinoids. In one embodiment, the method for rapid, sensitive and naked-eye detection of natural and/or synthetic cannabinoids in a sample comprises contacting the sample with a aptamer-based sensor selective for natural and/or synthetic cannabinoids, wherein the aptamer-based sensor comprises an aptamer that binds to natural and/or synthetic cannabinoids and a dye, e.g., a DNA-binding dye, for example, 3,3-di(3-sulfopropyl)-4,5,4,5-dibenzo-9-ethylthi-acarbocyanine (ETC) or 3,3'-di(3-sulfopropyl)-4,5,4',5'-dibenzo-9-methyl-thiacarbo-cyanine (MTC), and detecting whether a change in color occurs, the change in color being indicative of the presence of the natural and/or synthetic cannabinoids in the sample. Preferably, the aptamer comprises a nucleic acid sequence selected from SEQ ID Nos: 3, 6 and 9. In a specific embodiment, the cannabinoid is, for example, THC, THC-COOH, CBN, or THCV.

In some embodiments, the DNA-binding dye, e.g., ETC and MTC, may be used at a concentration ranging from about 0.01 µM to about 100 µM, from about 0.1 µM to about 90 µM, from about 0.1 µM to about 80 µM, from about 0.1 µM to about 70 µM, from about 1 µM to about 60 µM, from about 1 µM to about 50 µM, from about 1 µM to about 40 µM, from about 1 µM to about 30 µM, from about 1 µM to about 20 µM, or from about 1 µM to about 10 µM.

The method of the subject invention is remarkably simple, fast and specific. For example, the detection can be performed in a single tube containing the aptamer-based sensor and the sample of interest. In preferred embodiments, this colorimetric dye-displacement assay achieves instantaneous detections of as low as 3 µM target (e.g., THC) with the naked-eye.

Because the color intensity of the solution is proportional to the concentration of natural and/or synthetic cannabinoids, the method of the subject invention can be used to determine the concentration of natural and/or synthetic cannabinoids in the sample.

In one embodiment, the subject invention provides methods for detecting THC and/or a metabolite thereof, e.g., THC-COOH, in a sample. The method comprises contacting the sample with an aptamer-based sensor, wherein the aptamer-based sensor comprises a aptamer that binds to THC and/or a metabolite thereof and, optionally, a complementary nucleic acid sequence or a dye, and detecting THC and/or a metabolite thereof in the sample, wherein the detection comprises measuring a signal generated upon binding of THC and/or a metabolite thereof to the binding domain of the aptamer. Preferably, the aptamer comprises a nucleic acid sequence selected from SEQ ID Nos: 3, 6 and 9.

In one embodiment, the subject invention also provides methods for detecting XLR-11 and/or UR-144 in a sample. The method comprises contacting the sample with a aptamer-based sensor, wherein the aptamer-based sensor comprises a aptamer that binds to XLR-11, and/or UR-144 and, optionally, a complementary nucleic acid sequence or a dye, and detecting XLR-11 and/or UR-144 in the sample, wherein the detection comprises measuring a signal generated upon binding of XLR-11 and/or UR-144 to the binding domain of the aptamer. Preferably, the aptamer comprises a nucleic acid sequence selected from SEQ ID Nos: 4, 5, 7 and 24-25.

In one embodiment, the subject invention further provides methods for detecting one or more natural and synthetic cannabinoids in a sample. The method comprises contacting the sample with one or more aptamer-based sensors, wherein the one or more aptamer-based sensors comprise aptamers that bind to one or more specific natural and synthetic cannabinoids and, optionally, one or more complementary nucleic acid sequences, and detecting one or more natural and synthetic cannabinoids in the sample, wherein the detection comprises measuring signals generated upon binding of one or more natural and synthetic cannabinoids to the binding domain of the aptamers.

Other forms of detection of natural and/or synthetic cannabinoids as well as metabolites, derivatives, and mimetics thereof may also utilize the aptamers of the subject invention in, for example, electrochemical sensors, gold nanoparticle assays, enzyme linked aptamer sorbent assays (ELASA), pull down assays (immunoprecipitation), microplate/well assays, lateral flow assays and/or any other appropriate form of detection.

In some embodiments, the aptamer according to the subject invention may be used at a concentration from about 1 nM to about 10 mM, about 10 nM to about 5 mM, about 20 nM to about 2 mM, about 50 nM to about 1 mM, about 100 nM to about 500 µM, about 200 nM to about 200 µM, about 500 nM to about 100 µM, about 1 µM to about 50 µM, from about 1 µM to about 40 µM, from about 1 µM to about 30 µM, from about 1 µM to about 20 µM, from about 1 µM to about 10 µM, from about 2 µM to about 9 µM, from about 2 µM to about 8 µM, from about 2 µM to about 7 µM, from about 3 µM to about 6 µM, from about 4 µM to about 6 µM, and from about 5 µM to about 6 µM. In specific embodiments, the aptamer according to the subject invention may be used at a concentration of 1 nM, 10 nM, 20 nM, 25 nM, 50 nM, 100 nM, 200 nM, 500 nM, 1 µM, 2 µM, 3 µM, 4 µM, or 5 µM.

In one embodiment, the method according to the subject invention can achieve superior sensitivity for target detection at low micromolar or nanomolar concentration, for example, as low as about 200 µM, about 150 µM, about 100 µM, about 10 µM, about 1 µM, about 100 nM, about 10 nM, or about 1 nM.

In one embodiment, the methods for small molecule detection provided herein are rapid and can be completed in about 5 minutes to about 120 minutes, about 6 minutes to about 110 minutes, about 7 minutes to about 100 minutes, about 8 minutes to about 90 minutes, about 9 minutes to about 80 minutes, about 10 minutes to about 70 minutes about 15 minutes to about 60 minutes, about 20 minutes to about 50 minutes, or about 25 minutes to about 40 minutes. In some embodiments, the method can be completed in about 5 minutes, about 10 minutes, about 15 minutes, about 20 minutes, about 25 minutes, about 30 minutes, about 35 minutes, about 40 minutes, about 45 minutes, or about 50 minutes.

In another embodiment, the methods for small molecule detection provided herein are rapid and can be completed in about 5 seconds to about 5 minutes, about 10 seconds to about 4 minutes, about 15 seconds to about 3 minutes, about 20 seconds to about 2 minutes, or about 25 seconds to about 1 minute.

In one embodiment, the subject invention provides a method for detecting small molecules that are biomarkers for diagnosis of a disease or condition, or monitoring therapeutic response to specific treatments. In specific embodiments, the condition can be, for example, cancer, an injury, an inflammatory disease or a neurodegenerative disease. In some embodiments, the condition can be substance abuse, psychosis, schizophrenia, Parkinson's disease, attention deficit hyperactivity disorder (ADHD), and pain.

In one embodiment, the subject invention also further provides a kit for detecting natural and/or synthetic cannabinoids, the kit comprising the aptamer-based sensor according to the subject invention and instructions for using such aptamer-based sensor to detect natural and/or synthetic cannabinoids.

The subject invention encompasses the use of sequences having a degree of sequence identity with the nucleic acid sequence(s) of the present invention. A similar sequence is taken to include a nucleotide sequence which may be at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the subject sequence. Typically, the similar sequences will comprise the same or similar secondary structure as the subject nucleic acid aptamer. In one embodiment, a similar sequence is taken to include a nucleotide sequence which has one or several additions, deletions and/or substitutions compared with the subject sequence.

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof), such as "comprising," "comprises," and "comprise," can be used interchangeably.

The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

EXAMPLES

Experimental Section

Materials

All chemicals were purchased from Sigma Aldrich unless specified elsewhere. Cannabinoids and their metabolites including (−)-trans-Δ9-tetrahydrocannabinol (THC), 11-nor-9-carboxy-Δ9-tetrahydrocannabinol (THC-COOH), cannabinol (CBN), tetrahydrocannabivarin (THCV), tetrahydrocannabinolic acid (THCA), cannabidiol (CBD), cannabidiolic acid (CBDA), cannabigerol (CBG), cannabigerolic acid (CBGA), UR-144, XLR-11, UR-144 pentanoic acid metabolite (UR-144M), pentylone HCl, methcathinone HCl, α-pyrrolidinopentiophenone HCl were purchased from Cayman Chemicals.

Acetaminophen, alpha-tocopherol, albendazole, (±)-amphetamine hemisulfate, caffeine, clonazepam, cocaine HCl, granisetron, ibuprofen, (+)-methamphetamine HCl, nicotine, procaine HCl, (+)-pseudoephedrine HCl, tryptophan, and all other chemicals were purchased from Sigma-Aldrich unless otherwise noted. All DNA oligonucleotides were synthesized and HPLC-purified by Integrated DNA Technologies (IDT). Sequences of DNA used in this work are listed in Table 1. DNA were dissolved in PCR grade water before use and their concentrations were measured using a NanoDrop 2000 spectrophotometer (Thermo Fisher Scientific). Tween 20, formamide, SYBR Gold, streptavidin-coated agarose resin (capacity: 1-3 mg biotinylated BSA/ml resin), TOPO TA cloning kit, and ExoSAP-IT Express PCR Purification Kit were purchased from ThermoFisher Scientific. Peppermint, damiana, lemon balm, and thyme were purchased as dried leaves from online vendors.

Peppermint (Starwest Botanicals), damiana (herbandflame.net), lemon balm (Organic Bio Herbs, Ltd.), and thyme (Straight from France) were purchased as dried leaves from online vendors. Each leaf extract was prepared as below: 500 mg of each leaf was mixed with 10 mL methanol. After sonicated for 30 min at room temperature, the mixtures were left under 4° C. overnight for extraction. The mixture was then filtered with 0.22 μm syringe filter to remove insoluble contents. The final extracts (50 mg/mL) all showed a greenish-yellow color and were stored at 4° C.

TABLE 1

DNA sequences used in this work.

| Seq. ID | Sequence (5' to 3') |
|---|---|
| cDNA (SEQ ID No: 1) | TTTTTGTCGTAAGTTCTGCCATTTT/3STGBio/ |
| Library (SEQ ID No: 2) | CGAGCATAGGCAGAACTTACGAC(N30)GTCGTAAG AGCGAGTCATTC |

TABLE 1 -continued

DNA sequences used in this work.

| Seq. ID | Sequence (5' to 3') |
|---|---|
| THC1.2 (SEQ ID No: 3) | CTTACGACCCAGGGGGGTGGACAGGCGGGGGTTAGG GGGGTCGTAAG |
| XA1 (SEQ ID No: 4) | CTTACGACTGTGGTCGGGTGGTGGGCCTCTAGAGGG GTGTCGTAAG |
| XA2 (SEQ ID No: 5) | CTTACGACTGCGGGCATTTGTGGGGGCGTCGGTGG GCGTCGTAAG |
| F-THC1.2 (SEQ ID No: 6) | /5Cy5/GGCAGAACTTACGACCCAGGGGGTGGACA GGCGGGGGTTAGGGGGGTCGTAAG |
| F-XA1 (SEQ ID No: 7) | /5Cy5/GGCAGAACTTACGACTGTGGTCGGGTGGTG GGCCTCTAGAGGGGTGTCGTAAG |
| Q-cDNA (SEQ ID No: 8) | GTCGTAAGTTCTGC/3IAbRQsp/ |

/3STGBio/ biotin modification
/5Cy5/ Cy5 modification
/3IAbRQsp/ Iowa Black RQ quencher modification SELEX Procedure All aptamers were isolated from a 73-nt DNA oligo library. Each library strand is stem-loop structured with a 30 random nucleotide loop. The isolation of aptamers including positive, counter, parallel and serial selection was carried out following a previously reported library-immobilized SELEX protocol. Detailed selection conditions (e.g., amount of library strands, the concentration of target and counter target, and concentration of surfactant) for the THC and synthetic cannabinoid SELEX are provided in Table 2 and 3, respectively. All selections were performed in selection buffer (20 mM Tris-HCl, 0.5 mM $MgCl_2$, 20 mM NaCl, pH 7.4) unless stated otherwise. Aptamer sequence identification for THC- and synthetic-cannabinoid-binding aptamers were performed by Sanger sequencing and high throughput sequencing, respectively using the previously reported protocols.

TABLE 2

SELEX conditions for isolating a THC-binding aptamer.

| Round # | Pool size (pmole) | Counter-targets | | | | | Targets (nmole) |
|---|---|---|---|---|---|---|---|
| 1 | 1000 | N/A | | | | | 150 |
| 2 | 423 | 3 mg of each leaf extract (peppermint, damiana, lemon balm, or thyme) | | | | | 150 |
| 3 | 450 | 6 mg of each leaf extract | | | 225 nmole COC, PRC, PSE and ACM, 75 nmole IBU | 225 nmole AMP, PTL, MCA, and α-PVP, 75 nmole CLZ | 150 |
| 4 | 300 | 10 mg of each leaf extract | | | 450 nmole COC, PRC, PSE and ACM, 150 nmole IBU | 450 nmole AMP, PTL, MCA, and α-PVP, 150 nmole CLZ | 150 |
| 5 | 300 | | | | | | 150 |
| 6 | 300 | | | | | | 150 |
| 7 | 300 | 10 mg of each leaf extract | | | 750 nmole PRC, PSE andACM, 250 nmole IBU | 750 nmole AMP, PTL, MCA, and α-PVP, 250 nmole CLZ | 150 |
| 8 | 150 | | | | | | 150 |
| 9 | 150 | | | | | | 75 |
| 10 | 150 | | | | | | 75 |
| 11 | 150 | 10 mg of each leaf extract | 1.25 mL 50% saliva | 1.25 mL 50% urine | 750 nmole PRC, PSE and ACM, 250 nmole IBU | 750 nmole AMP, PTL, MCA, and α-PVP, 250 nmole CLZ | 75 | cocaine (COC), procaine (PRC), pseudoephedrine (PSE), acetaminophen (ACM), ibuprofen (IBU), amphetamine (AMP), pentylone (PTL), methcathinone (MCA), α-pyrrolidinopentiophenone (α-PVP), clonazepam (CLZ)

TABLE 3

SELEX conditions for the first, second, and third approaches for isolating a DNA aptamer that binds to both UR-144 and XLR-11.

| Approach # | Round # | Tween 20 | Pool size (pmole) | Counter-targets Matrices | Counter-targets Interferents | Incubation | Target |
|---|---|---|---|---|---|---|---|
| 1 | 1.1 | 0.05% | 1000 | N/A | N/A | N/A | 375 nmole XLR-11<br>375 nmole UR-144 |
|   | 2.1 |   | 500 | 1.25 mg each of peppermint, damiana lemon balm, and thyme extract | 225 nmole 5-HT, Trp, ABZ, TCP, THC, α-PVP, GNS, NIC, CAF, MET, and COC |   | 375 nmole XLR-11<br>375 nmole UR-144 |
|   | 3.1 |   | 500 | 3.75 mg each of peppermint, damiana lemon balm, and thyme extract | 225 nmole ABZ, TCP, and THC; 375 nmole 5-HT, Trp, α-PVP, GNS, NIC, CAF, MET, and COC |   | 225 nmole XLR-11<br>225 nmole UR-144 |
|   | 4.1 |   | 400 |   |   |   | 150 nmole XLR-11<br>150 nmole UR-144 |
|   | 5.1 |   | 400 |   |   |   | 225 nmole XLR-11<br>225 nmole UR-144 |
|   | 6.1 |   | 300 |   |   |   | 150 nmole XLR-11<br>150 nmole UR-144 |
| 2 | 1.2 | N/A | 1000 | N/A | N/A | N/A | 300 nmole XLR-11<br>300 nmole UR-144 |
|   | 2.2 |   | 600 | 1.25 mg each of peppermint, damiana lemon balm, and thyme extract | 75 nmole 5-HT, Trp, ABZ, TCP, THC, α-PVP, GNS, NIC, CAF, MET, and COC |   | 225 nmole XLR-11<br>225 nmole UR-144 |
|   | 3.2 |   | 500 | 3.75 mg each of peppermint, damiana lemon balm, and thyme extract | 225 nmole 5-HT, Trp, ABZ, TCP, THC α-PVP, GNS, NIC, CAF, MET, and COC |   | 225 nmole XLR-11<br>225 nmole UR-144 |
|   | 4.2 |   | 400 |   |   |   | 150 nmole XLR-11<br>150 nmole UR-144 |
|   | 5.2 |   | 250 | 7.5 mg each of peppermint, damiana lemon balm, and thyme extract | 225 nmole ABZ, TCP, and THC; 375 nmole 5-HT, Trp, α-PVP, GNS, NIC, CAF, MET, and COC | 10 min | 150 nmole XLR-11<br>150 nmole UR-144 |
|   | 6.2 |   | 250 |   |   |   | 150 nmole XLR-11 |
|   | 7.2 |   | 200 | 7.5 mg each of peppermint, damiana lemon balm, and thyme extract; 10 mg peppermint extract | 225 nmole ABZ; 375 nmole 5-HT, Trp, ABZ, TCP, THC, α-PVP, GNS, NIC, CAF, and MET; 750 nmole COC |   | 75 nmole UR-144 |
|   | 8.2 |   | 200 |   | 225 nmole ABZ; 375 nmole 5-HT, Trp, ABZ, TCP, THC, α-PVP, GNS, NIC, CAF, and MET; 750 nmole COC |   | 75 nmole UR-144 |
|   | 5.3 | N/A | 250 | 7.5 mg each of peppermint, damiana lemon balm, and thyme extract; 10 mg peppermint extract | 225 nmole ABZ; 375 nmole 5-HT, Trp, TCP, α-PVP, GNS, NIC, CAF, and MET; 600 nmole THC; 750 nmole COC |   | 150 nmole UR-144 |
|   | 6.3 |   | 250 |   |   |   | 150 nmole XLR-11 |
|   | 7.3 |   | 200 |   | 225 nmole ABZ; 375 nmole 5-HT, Trp, TCP, α-PVP, GNS, NIC, CAF, and MET; 750 nmole COC; 1200 nmole THC |   | 75 nmole UR-144 |
|   | 8.3 |   | 200 |   |   |   | 75 nmole XLR-11 |
|   | 9.3 |   | 150 |   | 225 nmole ABZ; 375 nmole 5-HT, Trp, TCP, α-PVP, GNS, NIC, CAF, and MET; 1250 nmole COC; |   | 150 nmole XLR-11 |
|   | 10.3 |   | 150 |   |   |   | 150 nmole XLR-11 |
|   | 11.3 |   | 150 |   |   |   | 150 nmole XLR-11 |
|   | 12.3 |   | 150 |   |   |   | 75 nmole XLR-11 |
|   | 13.3 |   | 150 |   |   |   | 3.75 nmole XLR-11 |
|   | 14.3 |   | 150 |   |   |   | 3.75 nmole XLR-11 |
|   | 15.3 |   | 150 |   |   |   | 75 nmole XLR-11 |
|   | 16.3 |   | 150 |   |   |   | 75 nmole XLR-11 |
|   | 17.3 |   | 100 |   |   |   | 37.5 nmole XLR-11 |

Serotonin (5-HT), tryptophan (Trp), albendazole (ABZ), tocophreol (TCP), tetrahydrocannabinol (THC), alpha-PVP (α-PVP), granisetron (IONS), nicotine (NIC), caffeine (CAF), cocaine (COC), methamphetamine (MET)

High Throughput Sequencing

The selection pool after round 16 and round 17 of synthetic cannabinoid SELEX were analyzed using Ion Torrent Sequencing as reported previously. The pools were prepared for sequencing as reported previously. Sequencing was performed at the FIU DNA Core Facility using an Ion Personal Genome Machine System with an Ion 318 v2 chip (ThermoFisher Scientific). The raw total reads for round 16 and round 17 were 681,673 and 526,186 respectively. The primer region of each sequence was first trimmed by cutadapt and the population of sequences from each pool were calculated using FASTAptamer. Clustering of the sequences was also performed by FASTAptamer using XA1 and XA2 as reference sequences. The XA1 and XA2 families are defined by those sequences which have no more than a 6-nucleotide difference (>80% similarity) from either XA1 or XA2, respectively.

Gel Elution Assay

Gel elution assay was performed using a previously described procedure. Briefly, the selection pool of interest was first hybridized with biotinylated cDNA and immobilized onto streptavidin-coated agarose beads. The beads were then washed with selection buffer and carefully aliquoted and incubated with different concentrations of the target for 60 min. The concentration of target-eluted strands in the supernatant and the remaining strands still immobilized on the beads were quantified using 15% denaturing polyacrylamide gel electrophoresis for each different target concentration to calculate the dissociation constants.

Isothermal Titration Calorimetry (ITC)

ITC experiments were performed using a MicroCal iTC200 Instrument (Malvern) at 23° C. Specifically, THC1.2, XA1, or XA2 in 300 µL of reaction buffer (20 mM Tris-HCl, 20 mM NaCl, 0.5 mM MgCl$_2$, 5% DMSO, pH 7.4) were heated at 95° C. for 10 minutes and immediately cooled down on ice before loading into the sample cell. The syringe was then loaded with an analyte dissolved in the same buffer and titrated into the sample cell. Each experiment consisted of an initial purge injection of 0.4 µL and 19 successive injections of 2 µL, with 300 sec spacing between every injection. The heat from each injection was integrated using the MicroCal analysis kit integrated into Origin 7 software, corrected with dilution heat obtained from analyte-to-buffer titrations, and fitted with a single-site binding model to calculate $K_D$s. The concentrations of aptamer and analyte and binding parameters for each titration is listed in Table 4.

TABLE 4

Concentrations of aptamer and analyte and binding parameters for ITC experiments.

| Experiment No. | Aptamer/ Concentration | Analyte/ Concentration | N (site) | $K_D$ (nM) |
|---|---|---|---|---|
| 1 | THC1.2/ 12 µM | THC/150 µM | 1.03 ± 0.01 | 46 ± 12 |
| 2 | THC1.2/ 20 µM | THC-COOH/ 300 µM | 0.44 ± 0.004 | 91 ± 18 |
| 3 | XA1/20 µM | XLR-11/200 µM | 0.96 ± 0.02 | 310 ± 70 |
| 4 | XA1/20 µM | UR-144/150 µM | 0.91 ± 0.01 | 127 ± 32 |
| 5 | XA2/20 µM | XLR-11/200 µM | 0.81 ± 0.02 | 394 ± 93 |
| 6 | XA2/20 µM | UR-144/150 µM | 0.70 ± 0.01 | 170 ± 44 |

Fluorophore-Quencher Assay

The fluorophore-quencher assay was performed as previously described with some modification. First, the affinity of F-THC1.2 and F-XA1 to Q-cDNA was characterized. Specifically, F-THC1.2 or F-XA1 (final concentration 40 nM) and different concentrations of Q-cDNA (final concentration 0, 3.1, 6.3, 12.5, 25, 37.5, 50, 75, 113, and 150 nM for F-THC1.2 and 0, 6.3, 12.5, 25, 500, 75, 100, 150, 225, and 300 nM for F-XA1) were mixed in 80 µL of reaction buffer (20 mM Tris-HCl, 20 mM NaCl, 0.5 mM MgCl$_2$, 5% DMSO, pH 7.4). The samples were then heated 95° C. for 5 min and cooled to 25° C. at a rate of 0.1° C./s on a thermal cycler. After an additional 5 min at room temperature, 75 µL of each sample was loaded into a 96-well plate, and the fluorescence intensity of each sample ($\lambda_{ex}$=648 nm, $\lambda_{em}$=668 nm) were recorded using a Tecan M1000 Pro plate reader. The concentration of unbound aptamer for each sample was calculated by F/F$_0$×50 nM, where F and F$_0$ is the fluorescence of the sample in the presence and absence of Q-cDNA respectively. The free Q-cDNA concentrations for each sample was then calculated by $C_Q$–F/F$_0$×50 nM, where $C_Q$ is the total concentration of Q-cDNA added to each sample. The fluorescence of each sample was plotted against the free concentration of Q-cDNA. The dissociation constant ($K_D$) between F-THC1.2 and Q-cDNA ($K_{D1}$) was determined by the concentration of free Q-cDNA where half of the fluorescence was quenched.

A second experiment was used to quantify the affinity of the target to the aptamer-cDNA complex. Specifically, F-THC1.2 or F-XA1 (final concentration 40 nM) and Q-cDNA (final concentration 125 nM for F-THC1.2 and 300 nM for F-XA1) were mixed in reaction buffer and the solution was heated and cooled as mentioned previously. Different concentrations of analyte (THC or THC-COOH for F-THC1.2 and UR-144 or XLR-11 for F-XA1) were then mixed with the aptamer-cDNA complex and incubated for 30 min at room temperature. The final samples were loaded into a 96-well plate (total volume 75 µL), and the fluorescence of each sample at 668 nm (with excitation at 648 nm) was recorded and plotted against the target concentration and fitted with the dose-response curve to determine the EC$_{50}$ concentrations, where half of the fluorescence was recovered. The $K_D$ between the target and aptamer-cDNA complex ($K_{D2}$) was calculated by C$_{50}$/EC$_{50}$, where C$_{50}$ is the free Q-cDNA concentration when EC$_{50}$ is reached. C$_{50}$ is 105 nM and 280 nM for F-THC1.2 and F-XA1, respectively. Finally, the $K_D$s between the targets and free aptamer were calculated by $K_{D1}$/$K_{D2}$. For fluorescence-based sensing of analytes, sensor performance was assessed using signal gain. The signal gain of each sample was calculated by (F–F$_0$)/F$_0$×100% where, where F is the fluorescence obtained at 668 nm in the presence of varying concentrations of target and F$_0$ is the fluorescence obtained without analyte. Each experiment was performed three times. The limit of detection of the assay was determined by the lowest analyte concentration that yielded an average signal greater than three times its standard deviation.

For characterization of aptamer specificity, aptamer-cDNA mixtures were first prepared as described above. 10 or 50 µM of different analytes were then mixed with the aptamer-cDNA complex and incubated for 30 min at room temperature. The final samples were loaded into a 96-well plate (total volume 75 µL), and the fluorescence spectra of each sample were recorded at room temperature. The signal gain of each sample was calculated as described above. The cross-reactivity of each analyte was calculated based on their signal gains, where the signal gain of 10 µM THC and UR-144 was defined as 100% cross-reactivity for F-THC1.2 and F-XA1, respectively.

TABLE 5

Sequences of the random region and count for each clone from the round 11 THC SELEX pool.

| No. | Sequences (5'-3') | Counts (total 44) | SEQ ID No. |
|---|---|---|---|
| 1 | CCAGGGGGTGGACAGGCGGGGGTTAGGGG | 30 | SEQ ID No: 9 |
| 2 | CCAGGGGGTGGACAGACGGGGGTTAGGGG | 1 | SEQ ID No: 10 |
| 3 | CCAGGGGGTGGACAGGCGGGGGTCAGGGG | 1 | SEQ ID No: 11 |
| 4 | CATGCCGACACCTTCAGAAGGTTCAGCGGA | 1 | SEQ ID No: 12 |
| 5 | CGGGCTGTCAACTGGGGAGTGCGGACTGGT | 1 | SEQ ID No: 13 |
| 6 | AACTGAGGCGGACAGAAGGGATCCGCGTGG | 1 | SEQ ID No: 14 |
| 7 | GCGGCTGGAGCGTTAGGTCTCAAGGATAGG | 1 | SEQ ID No: 15 |
| 8 | GAGGAGACCTACCATTGTGACGGTAACGTT | 1 | SEQ ID No: 16 |
| 9 | CACCAGTGAGCCTCCCGGGATCGTGAAATG | 1 | SEQ ID No: 17 |
| 10 | ACGGATAACCCACGTGTATAGGTTGGAGTG | 1 | SEQ ID No: 18 |
| 11 | AGGGTAGAGCCTGATCAAGTGGTGAATTCT | 1 | SEQ ID No: 19 |
| 12 | GGCCTGTGTGCGGTCATTGACGCTGGCGCT | 1 | SEQ ID No: 20 |
| 13 | TGCGTACGTAAACTGTTTTGTTTGACCGTA | 1 | SEQ ID No: 21 |
| 14 | CGGATCAGCATACGTTGCGTAGTCCAACTG | 1 | SEQ ID No: 22 |
| 15 | GTTCGGTAGAGCTAGAATTGTGGCGGTGAC | 1 | SEQ ID No: 23 |

Dye-Displacement Assay for Colorimetric Detection of THC.

For THC detection, 3.1 µL, of 142 µM THC1.2 was incubated in 51.3 µL Tris-HCl buffer solution (Final concentration: 10 mM Tris-HCl, pH 7.4) for 5 min. Then, 0.8 µL of 1% Triton-X100 (w/v) and 0.8 µL of 400 µM ETC (dissolved in 100% DMSO) was added to the aptamer solution and incubated for 1 min. Subsequently, 16 µL of salt solution (Final concentrations: 20 mM NaCl and 0.5 mM MgCl$_2$) was added. Immediately afterwards, 8 µL of 55% DMSO or varying concentrations of $\Delta^9$-tetrahydrocannabinol (THC) dissolved in 55% DMSO (Final concentrations: 0.25, 0.5, 1, 1.5, 2, 2.5, 3.5, 5, 10, or 20 µM) were added to the reaction mixture, and 75 µL of the resulting solution was loaded into the wells of a transparent 384-well plate. UV-vis spectra were recorded from 400-800 nm using a Tecan Infinite M1000 Pro. Area under the curve was calculated using Origin software for the dye monomer (Area 1, 500-620 nm) and dye aggregate (Area 2, 620-680 nm). Signal gain was calculated using $(R-R_0)/R_0$, where R and $R_0$ is the ratio Area 2/Area 1 with and without THC, respectively. To determine the cross reactivity of assay, the same procedure was performed for 5 µM THC, THC-COOH, THCV, and CBN, 25 µM THCA, CBD, CBDA, CBG, CBGA, UR-144, or XLR-11, and 100 µM cocaine, amphetamine, heroin, α-pyrrolidinovalerophenone, methamphetamine, pentylone, procaine, acetaminophen, ibuprofen, nicotine, caffeine, clonazepam, and fentanyl. Cross reactivity was calculated relative to the signal gain produced by 5 µM THC.

Example 1—Isolation of THC-Binding DNA Aptamer

Numerous aptamers have been isolated for various small molecules. However, it has been challenging to isolate aptamers for small molecules with a limited number of epitopes or low water-solubility. The limitations of natural DNA libraries were explored by isolating aptamers in vitro against three low-epitope hydrophobic small molecule targets: (−)-trans-$\Delta^9$-tetrahydrocannabinol (THC), UR-144 and XLR-11 (FIG. 1) via SELEX.

To investigate whether there are limitations in isolating aptamers with high affinity and specificity for challenging hydrophobic targets such as THC from unmodified DNA libraries, and to determine the extent of the influence that the selection conditions have on the outcome of SELEX, previously reported stem-loop structured library containing 30 random nucleotides in combination with the library-immobilized SELEX method was used for aptamer isolation. This selection procedure has successfully yielded aptamers targeting various small molecules including steroid hormones, neurotransmitters, and synthetic cathinones. Notably, the library according to the subject invention is immobilized on a solid support, whereas the target is free in solution.

Figure 2A:
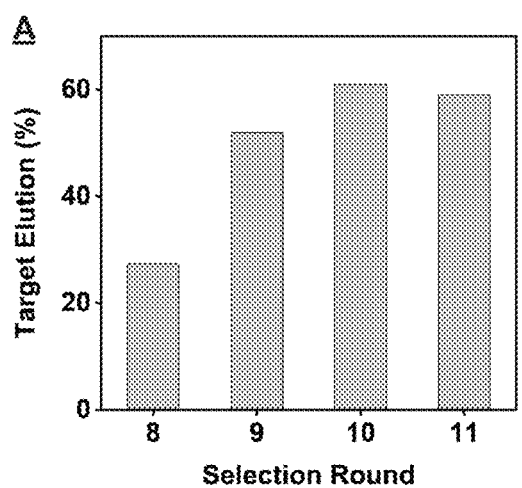
FIGS. 2A-2C show the characterization of selection pools during SELEX using a gel elution assay. (A) Fraction of the enriched pools from Round 8 to Round 11 eluted by 100 μM THC. (B) Fraction of the final Round 11 pool eluted by 0, 5, 10, 25, 50, 100, 200 μM THC was used to determine target binding affinity of the enriched pool. (C) Fraction of the Round 11 enriched pool eluted by 50 μM THC or THC-COOH or 300 μM cocaine, methamphetamine, procaine, pseudoephedrine, acetaminophen, amphetamine, pentylone, or α-PVP, 200 μM ibuprofen or clonazepam, or 0.16 mg/mL extract of peppermint, damiana, lemon balm, or thyme.
Figure 2B:
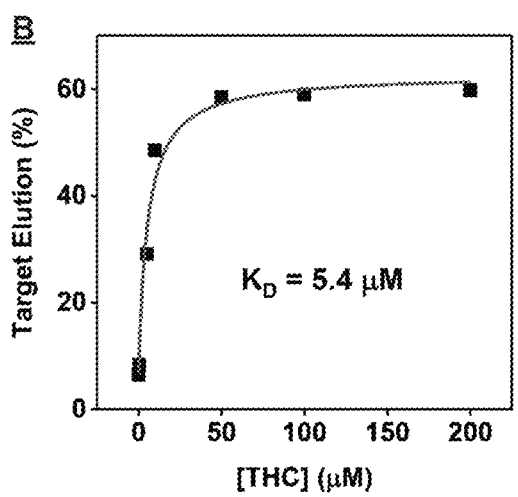
Figure 3A:
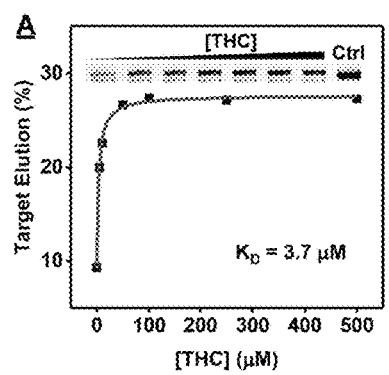
FIGS. 3A-3C show the THC-binding affinity of the pools after Round (A) 8, (B) 9, and (C)10 determined using the gel-elution assay. The inset is a gel image of the pool eluted by various concentrations of THC.
Figure 3B:
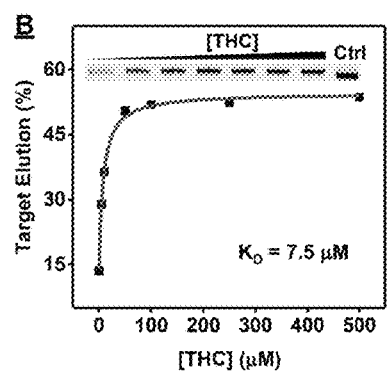
Figure 3C:
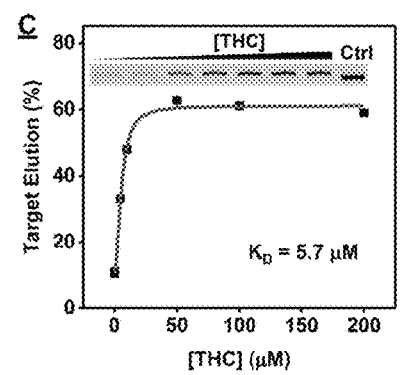

In total, 11 rounds of selection were performed. Specifically, in the first eight rounds of selection, a higher target concentration (200 µM) was used to ensure all strands binding to THC were enriched (Table 2). Notably, 2.6% methanol was included in the selection buffer to completely dissolve THC. After 8 rounds of selection, a reported gel elution assay was used to evaluate the target-binding affinity of the enriched pool. It is found that 27% of the library can be eluted with 100 µM THC (FIG. 2A). The $K_D$ of the pool towards THC was 3.7 µM (FIG. 3A). The selection stringency was then increased by reducing the target concentration to 100 µM in Round 9 and 50 µM in Rounds 10 and 11 to isolate aptamers with high affinity (Table 2). The fraction of the target-eluted library increased in Round 9 to 52% and further rose to 61% in Round 10 and 59% in Round 11 (FIG. 2A), while the $K_D$ of these pools did not significantly differ from the Round 8 pool (FIGS. 2B, 3B and 3C). Thus, high-affinity aptamers had been sufficiently enriched.

Unlike other illicit drugs which are fully synthetic (e.g. fentanyl) or extracted from natural sources (e.g. morphine), cannabinoids are typically found within and consumed as dried plant material (i.e. marijuana) or crude plant extract (i.e. hashish oil). Meanwhile, *cannabis* is commonly blended with other herbs for smoking.

To remove non-specific aptamers binding to endogenous compounds in these herbs, counter-SELEX was performed from Rounds 2 to 11 against methanolic extracts of four different herbs (i.e. pepper mint, damiana, lemon balm, and thyme) that are commonly blended with *cannabis*. From Round 3 to Round 11, drugs commonly abused with marijuana (cocaine, clonazepam, methamphetamine, amphetamine, pentylone, α-PVP, and ibuprofen) and common drug adulterants (procaine, acetaminophen, and pseudoephedrine) were also included as counter-targets. The amount of counter-target used in each round was gradually increased until the final round to increase the stringency of counter-SELEX (Table 2).

Figure 2C:
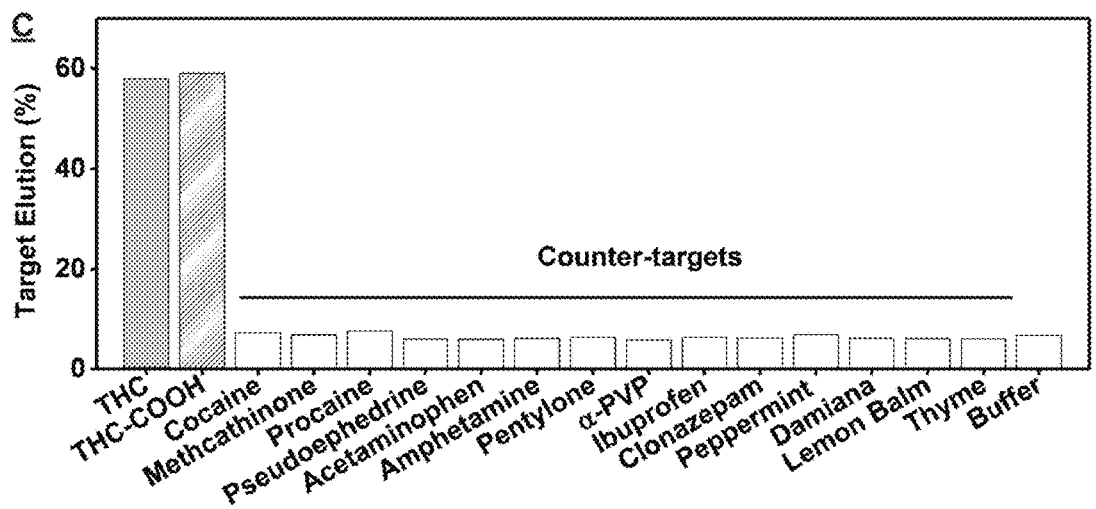

Finally, in Round 11, 50% urine and 50% saliva were included in counter-SELEX to remove strands binding to any interferents existing in these biomatrices (Table 2). After the final round, the gel elution assay was used to characterize the specificity of the selection pool. While 59% of library could be eluted with 50 µM THC, similar elution as buffer (7%) was observed with 200 µM ibuprofen and clonazepam, 500 µM of cocaine, methcathinone, procaine, pseudoephedrine, acetaminophen, amphetamine, pentylone, and α-PVP, or 0.16 mg/mL pepper mint, damiana, lemon balm, and thyme extract (FIG. 2C).

These results demonstrated that the aptamers in the final enriched pool have high specificity to THC. Notably, the pool was also cross reactive to 11-nor-9-carboxy-$\Delta^9$-tetrahydrocannabinol (THC-COOH) (FIG. 2C), the major metabolite of THC. In an analytical context, this is favorable as it enables the use of the aptamer for the evaluation of marijuana consumption by detecting this compound in urine. Also, simultaneous detection of THC and its metabolites by the aptamer increases the assay sensitivity and detection window in saliva.

Figure 4A:
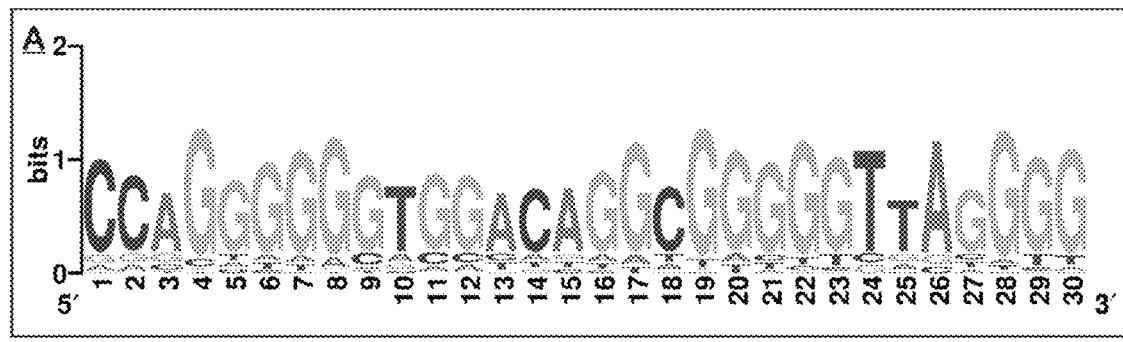

The Round 11 pool was therefore sequenced by cloning and Sanger sequencing. The pool was found to have very low diversity (FIG. 4A), and only one consensus sequence was found. Among the 49 clones, 35 of them had an identical sequence, which is termed THC1.2 (Table 5). THC1.2 has a stem-loop structure, and is G-rich (FIG. 5). This is commonly observed for hydrophobic small molecule-binding aptamers.

Example 2—Characterization of the Isolated THC-Binding Aptamer

THC1.2 was then synthesized and a fluorescence assay and isothermal titration calorimetry (ITC) were used to characterize the target-binding affinity of the aptamer. Both methods are well established for measuring aptamer affinity for small molecules with $K_D$ of 10 nM-1 mM.

Figure 4B:
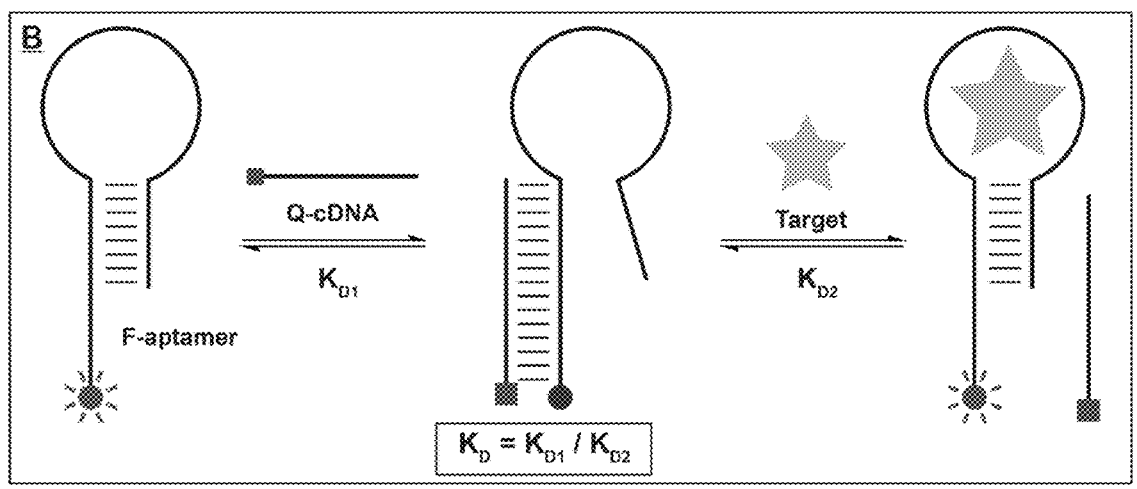

The high target-binding affinity of THC1.2 was first confirmed using a strand-displacement fluorescence method. The calculation of the binding affinity of target to the aptamer requires determining the affinity of the aptamer to a complementary DNA strand ($K_{D1}$) and the affinity of the target towards the aptamer-cDNA complex ($K_{D2}$). Specifically, the Cy5-labeled aptamer (F-THC1.2) and an IowaBlack RQ-labeled complementary DNA strand (Q-cDNA) were synthesized. When the aptamer is free in solution, the fluorophore emits strong fluorescence. However, when the aptamer hybridizes with its Q-cDNA, the quencher is brought into close proximity to the fluorophore, and fluorescence greatly decreases. When challenged with the target, the aptamer binds to the target and dissociates from Q-cDNA, resulting in recovery of fluorescence (FIG. 4B). $K_{D1}$ was determined by titrating different concentrations of Q-cDNA into a solution of aptamer (FIG. 4C). $K_m$ was calculated to be 4.6 nM. $K_{D2}$ was then measured by titrating the target into a solution of aptamer-cDNA complex (FIG. 4D). $K_{D2}$ was found to be 0.13. Finally, the affinity of the free aptamer for THC was calculated by the expression $K_{D1}/K_{D2}$, which equaled 34.2 nM. The affinity of the aptamer to THC-COOH was measured to be similarly high with a $K_D$ of 114 nM (FIG. 6).

ITC was then used to confirm the binding affinity of THC1.2 to THC and THC-COOH. As expected, the results showed that THC1.2 binds to THC and THC-COOH with a $K_D$ of 46±12 nM and 91±18 nM, respectively (FIG. 7). Therefore, the binding affinities attained through ITC are well-corroborated with the fluorescence assay.

Figure 8A:
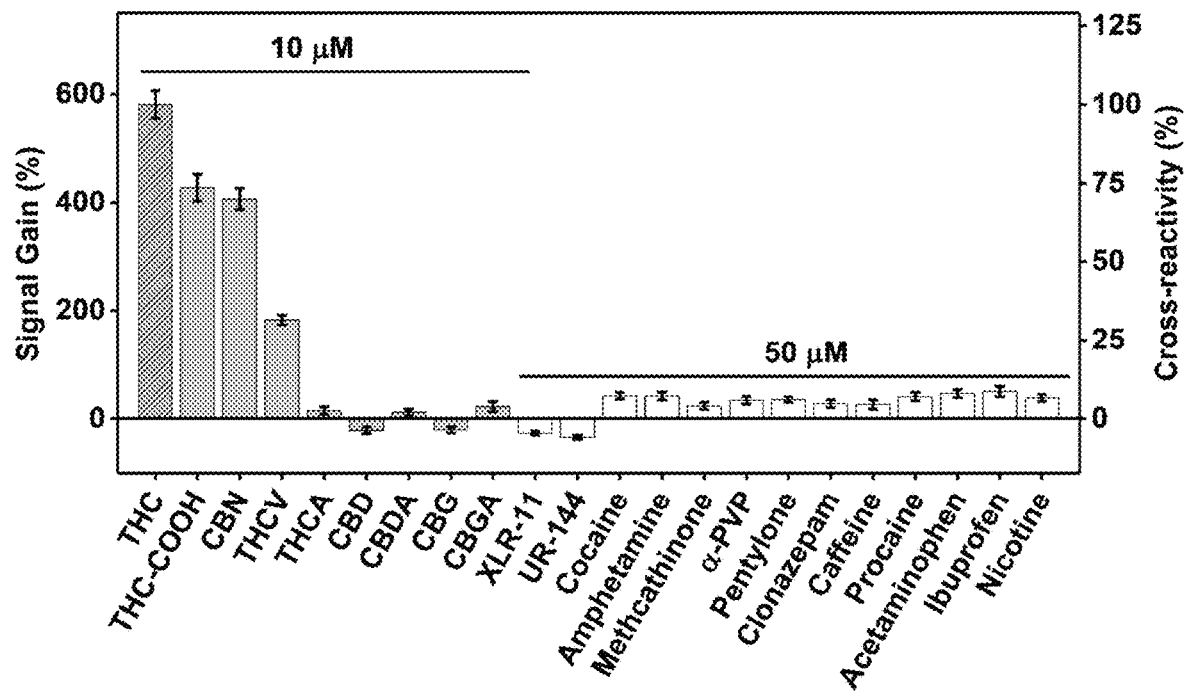
FIGS. 8A-8B show the specificity of THC1.2 for cannabinoids and interferers. (A) Signal gains produced by different cannabinoids and interferers, and their cross-reactivity relative to THC in the strand-displacement fluorescence assay. (B) Structures of different cannabinoids structurally-related to THC.
Figure 8B:
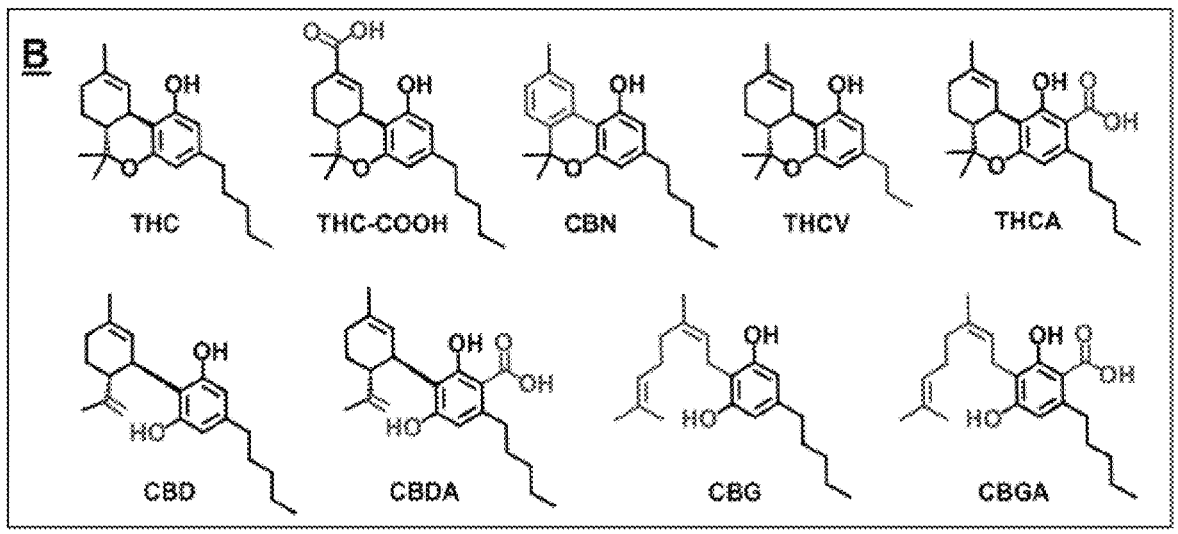

The same fluorescence assay was further used to characterize the specificity of THC1.2. The aptamer's cross-reactivity was first assessed to other major cannabinoids including THC-COOH, tetrahydrocannabinolic acid (THCA), tetrahydrocannabivarin (THCV), cannabigerolic acid (CBGA), cannabidiolic acid (CBDA), cannabigerol (CBG), cannabidiol (CBD), cannabinol (CBN) at a concentration of 10 µM (FIG. 8). The results showed that the aptamer is cross-reactive to THC-COOH, CBN and THCV, but does not bind to other cannabinoids. Structure-activity relationships showed that alteration of substituents at the aromatic ring or opening of the ether group completely impairs aptamer recognition, which implies that these functional groups are involved in target binding.

Based on this finding, it appears that the binding mechanism of THC1.2 and C11.41 are different, because C11.41 tolerates alterations to the aromatic moiety of THC. Shortening of the alkyl tail results in a great reduction in affinity, which implies that the size and shape of the ligand plays a role in binding. On the other hand, modification of the cyclohexene ring only moderately reduces binding affinity, indicating less involvement of these regions in aptamer binding.

Figure 9A:
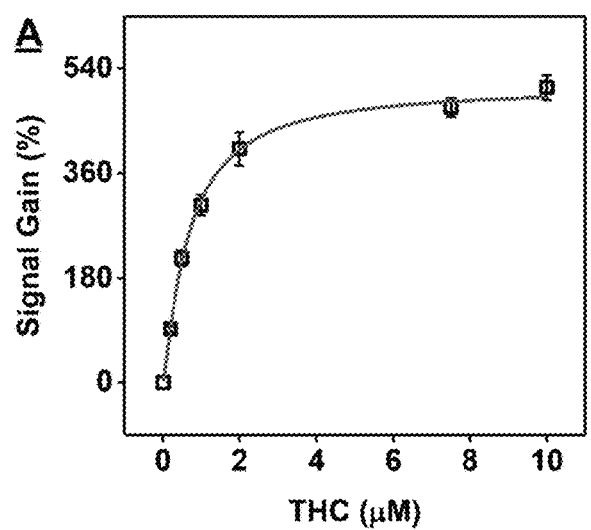
FIGS. 9A-9B show the calibration curve of THC1.2 for (A) THC and (B) THC-COOH based on the strand-displacement fluorescence assay.
Figure 9B:
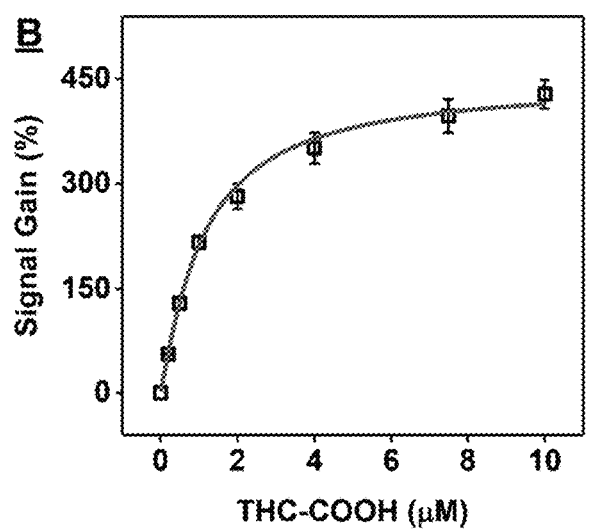

To demonstrate the excellent specificity of the aptamer, THC1.2 was challenged with 15 interferents including common illicit drugs (XLR-11, UR-144, cocaine, methamphetamine, amphetamine, methcathinone, α-PVP, and pentylone), pharmaceuticals (clonazepam, pseudoephedrine, acetaminophen, and ibuprofen), cutting agents (caffeine and procaine), and nicotine. All interferents showed less than 10% cross-reactivity at a 5-fold higher concentration relative to 10 µM THC. Notably, the synthetic cannabinoids XLR-11 and UR-144, which also bind to cannabinoid receptors of the human body (CB1 and CB2), do not bind to THC1.2, demonstrating the different recognition mechanism of this aptamer compared with these receptors. These results clearly demonstrated that high-affinity aptamers with excellent specificity can be generated from unmodified DNA libraries even for targets as challenging as THC. The superior binding characteristics of THC1.2 allows for sensitive fluorescence detection of THC. Using the above-described strand-displacement fluorescence assay, both THC and THC-COOH can be easily detected at a concentration of 200 nM (FIG. 9). Given that the concentration of THC in oral fluids is usually above 300 nM within two hours of consumption, and THC-COOH can be detected in urine at 200 nM many hours after consumption, THC1.2 can be used for onsite detection of recent *cannabis* use in both urine and saliva samples.

Example 3—Isolation of a DNA Aptamer that Binds to Both UR-144 and XLR-11

To further probe the limits of unmodified libraries, an aptamer binding to UR-144 and XLR-11, two widely-abused synthetic cannabinoids with high structural similarity were isolated. In terms of functional groups available for aptamer binding, these targets contain only an indole ring, a ketone, pentyl tail, and tetramethylcyclopropyl ring. No aptamer has been isolated for these targets, or any small molecule with so few functional groups with an unmodified library.

The same library-immobilized SELEX procedure, the library described above and the previously-reported parallel-and-serial selection strategy were used to isolate an aptamer capable of binding both UR-144 and XLR11. Overall, it took three different approaches before an aptamer could be isolated binding to UR-144 and XLR-11 with high affinity and specificity.

Figure 10:
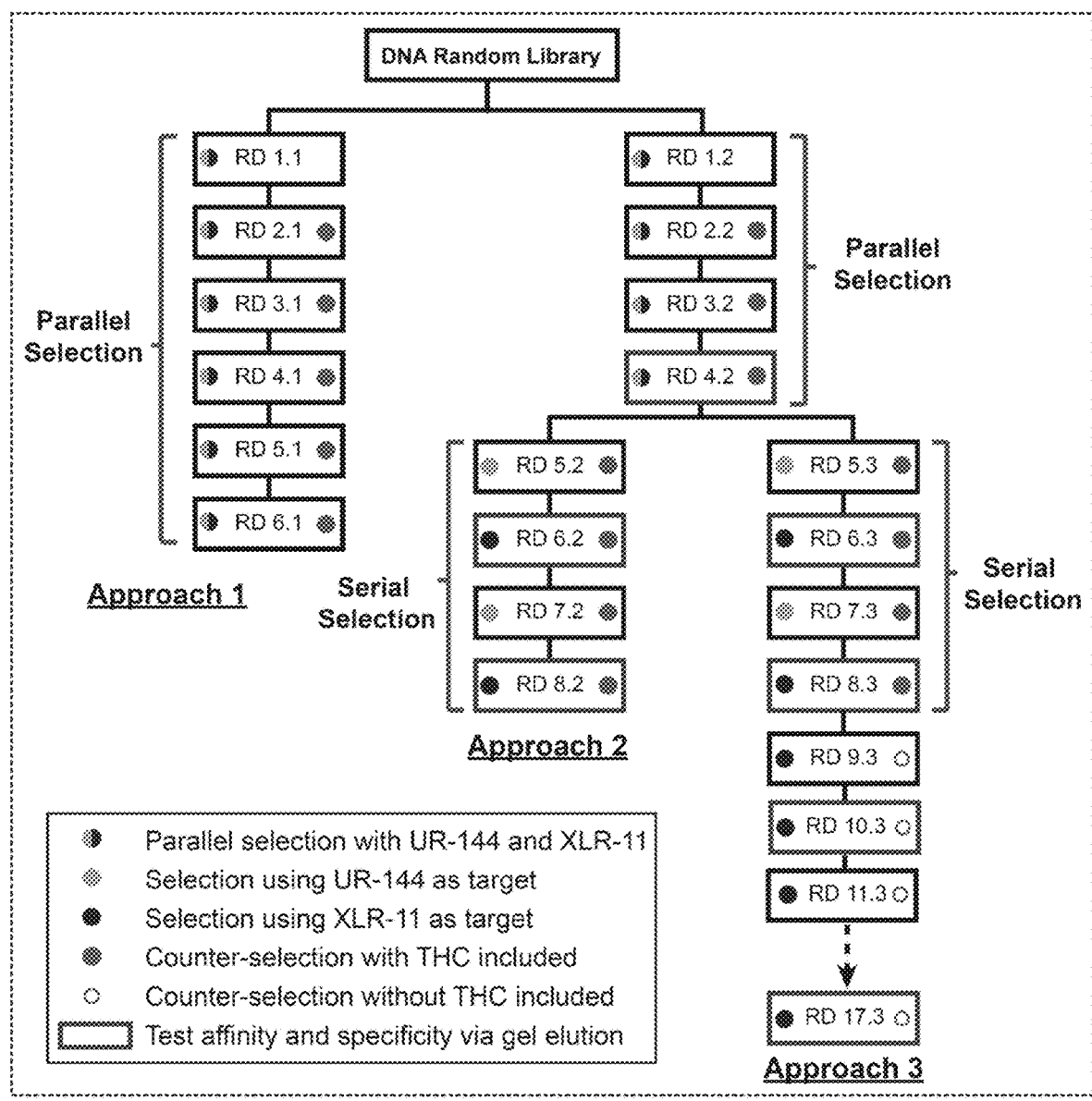
FIG. 10 shows SELEX road map for isolating an aptamer binding UR-144 and XLR-11 using three different approaches.

The road map of SELEX is shown in FIG. 10. First, in parallel selection, SELEX is performed with each target to accumulate binders to these targets individually. These parallel pools are then combined for serial selection, where the pool is challenged with each target consecutively to isolate aptamers that are capable of binding both targets. In the first approach (FIG. 10, RD 1.1-RD 6.1), six rounds of parallel selection were performed with UR-144 and XLR-11. Realizing that the targets have extremely low water solubility but high solubility in DMSO (>100 mM), 5% DMSO and 0.05% (v/v) Tween 20 were included to increase their solubility in the selection buffer. The detailed selection conditions for the first approach is listed in Table 3.

In the first round, low selection stringency was employed with a large library size (1000 pmole) and relatively high target concentration (500 µM) to prevent loss of potential aptamers. As SELEX progressed, the library size and target concentration were gradually reduced to enrich high-affinity aptamers (Table 3). Additionally, to enhance aptamer specificity, from the second round on, counter-SELEX was performed against plant extracts (leaves of damiana, lemon balm, mint, and thyme), commonly-used drugs (nicotine, caffeine, cocaine, methamphetamine, α-PVP, and THC), and structurally-similar compounds (serotonin, tryptophan, tocopherol, albendazole, and granisetron) (Table 3). Unfortunately, no specific target elution was observed in either pool after 6 rounds of selection. The addition of Tween 20 might have been deleterious for aptamer isolation. Given that the concentration of Tween 20 employed was above the critical micelle concentration (0.007%, v/v), target molecules could have potentially been trapped in micelles, effectively preventing their interaction with library strands. The surfactant may have also increased non-specific elution of library strands, which reduced selection efficiency.

For the second approach (FIG. 10, RD 1.2-RD 8.2), Tween 20 was removed from the selection buffer. SELEX was performed with the same generally strategy with minor modifications (Table 3). After four rounds of parallel selection, significant target elution was observed in each individual parallel pool. This clearly demonstrated that Tween 20 precluded the enrichment of aptamers binding to the targets and should have been excluded for selection. Accordingly, these two pools were combined (FIG. 10, RD 4.2) and the target-binding affinity and specificity of this pool was characterized using the gel-elution assay. The pool had high binding affinity for XLR-11 ($K_D$=49 04) (FIG. 11A), high cross reactivity to UR-144 (86%), and no cross-reactivity to most of the counter-targets (FIG. 11B). However, it still showed moderate cross-reactivity to THC (18%) and significant cross-reactivity to the plant extracts (data not shown), suggesting the use of more stringent counter-SELEX conditions in subsequent rounds. From the fifth round, the combined pool was used to perform serial selection (FIG. 10, RD 5.2-RD 8.2) to rapidly isolate an aptamer that recognizes both targets. Specifically, selection was performed with UR-144 on Rounds 5.2 and 7.2 and XLR-11 on Rounds 6.2 and 8.2. After round 8.2, the target-binding affinity and specificity of the pool was characterized using the gel-elution assay. The result shows that XLR-11-binding affinity of the RD 8.2 pool was 51 µM (FIG. 12A), similar as Round 4, and cross-reactivity to UR-144 was 107%. However, the pool was now strongly cross-reacting to THC (129%) (FIG. 12B).

Figure 12C:
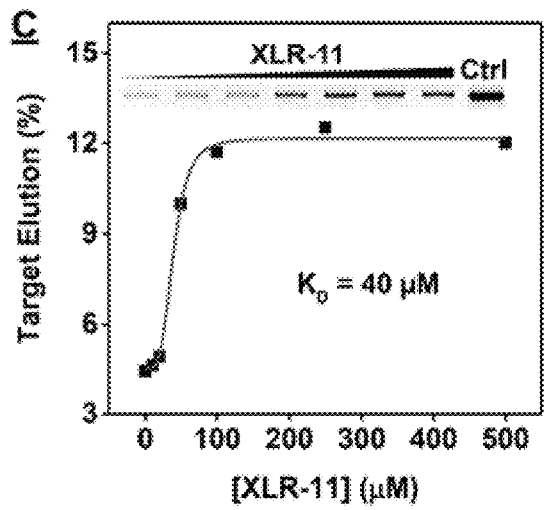
Figure 12D:
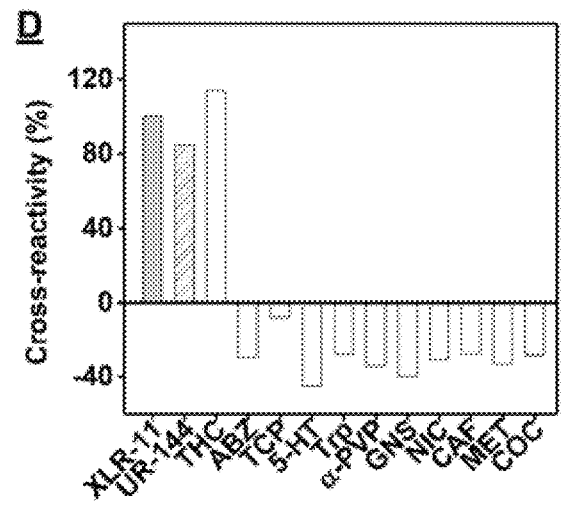

Apparently, the pool was binding to THC with greater affinity than the selection targets. To remedy this, serial selection was restarted from the round 4 combined pool (FIG. 10, RD 4.2) (see third approach FIG. 10) (FIG. 10, RD 5.3-RD 17.3) with positive target selection remaining the same as before but higher counter-SELEX stringency, particularly against THC (Table 3). After serial selection from RD 5.3-RD 8.3, the number of washes during counter-SELEX was increased from three to eight in round 5 and 6 and sixteen in round 7 and 8 to remove interferent binders. In addition, from round 6 to 8, a pre-treatment strategy where the library was incubated with THC overnight prior to immobilization was used. THC-bound strands would be unable to duplex with cDNA employed for bead immobilization, thereby excluding them from the SELEX process. The target-binding affinity and specificity of the round 8 (RD 8.3) pool was characterized. Although the pool bound to XLR-11 with $K_D$ of $40_R$M and UR-144 as well, even with extremely stringent counter-SELEX against THC, the pool still had markedly high cross-reactivity to this interferent (114%) (FIGS. 12C and 12D). It is hypothesized that THC was being retained in the library-containing column, even after extensive washing with buffer, due to its high hydrophobicity and viscosity. This caused strands binding to THC to be retained and enriched. Removing THC as a counter-target would reduce enrichment of THC-binding sequences. Therefore, from the ninth round (RD 9.3), performing counter-SELEX against THC was ceased.

Figure 12E:
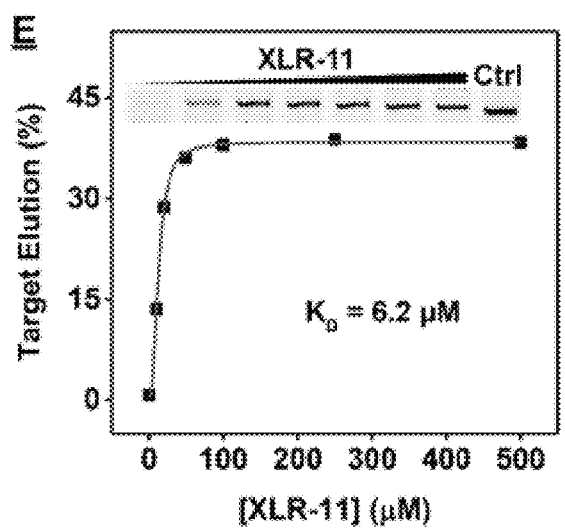
Figure 12F:
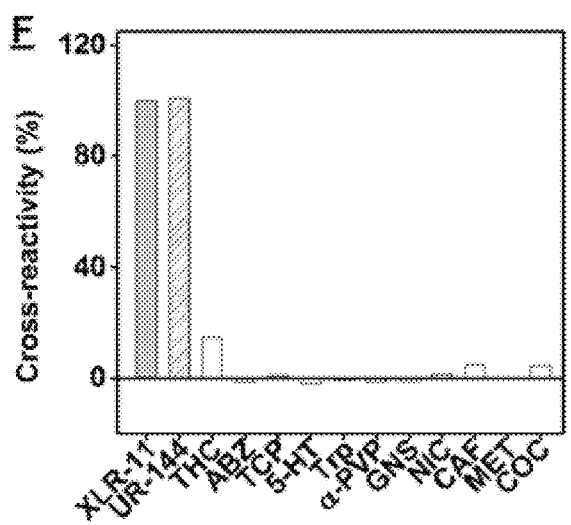

In addition, from this round on, XLR-11 was used as the sole target since the RD 8.3 pool cross-reacted well to both targets. For the next several rounds, XLR-11-related pool elution increased, pool affinity improved, and cross-reactivity to UR-144 remained high (FIGS. 13A-C). Meanwhile, the cross-reactivity to THC greatly decreased (FIG. 13D), confirming the hypothesis regarding THC contamination. Pool elution did not further change at round 17, and the target-binding affinity and specificity of this pool (RD 17.3) were therefore characterized (FIG. 12E). The high XLR-11-binding affinity ($K_D$=6.2 µM), high cross-reactivity to UR-144 (101%), and high specificity against all counter-targets, including THC (15%) (FIG. 12F) were observed.

Figures 14A, 14B, 14C:
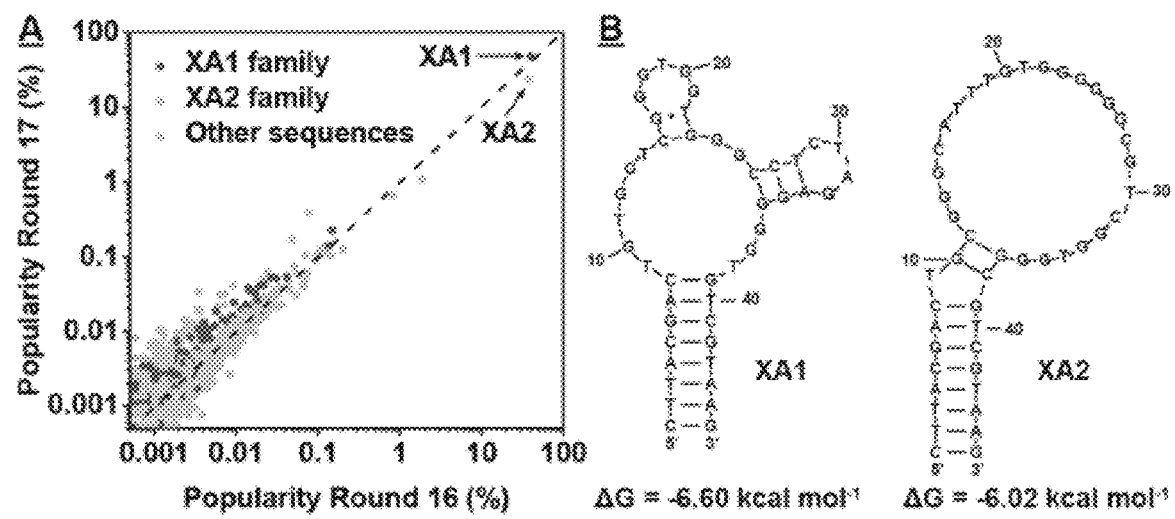

Next, next-generation sequencing of the round 16 and 17 pool was performed because the population of target-binding sequences was only 38% (FIG. 12E). The round 16 and 17 pools respectively had 90,341 and 93,680 unique sequences and 681,673 and 526,186 total reads. Cutadapt was used to cluster these sequences to find consensus sequences. The sequences that were the most popular in both rounds (XA1 and XA2) (FIG. 14A) were identified. Based on these two aptamers, two families were found that had at least 80% sequence homology (i.e. 6 nucleotides or less mutations). The XA1 and XA2 families consisted of 43% and 40% of the round 16 pool, respectively. An increase in the prevalence of the XA1 family (50%) and a significant decrease in the XA2 family (17%) was observed in round 17.

Example 4-Characterization of XA1 and XA2

Figure 15C:
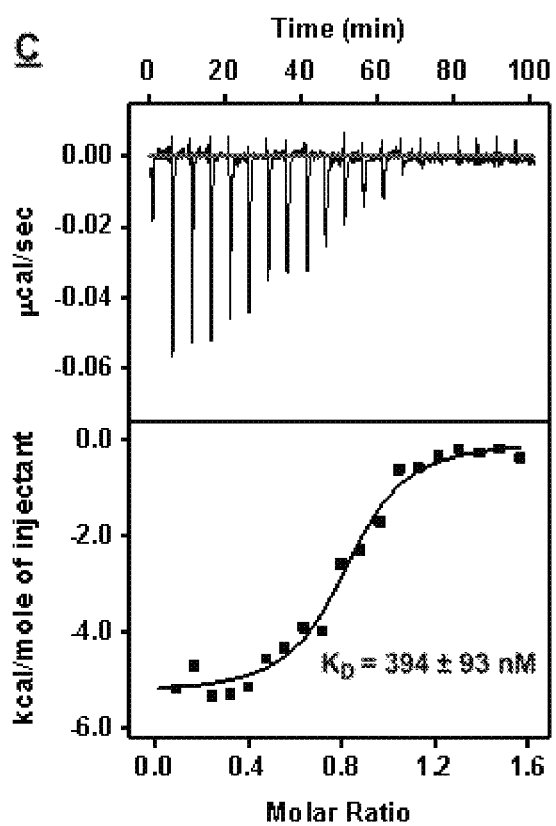
Figure 15D:
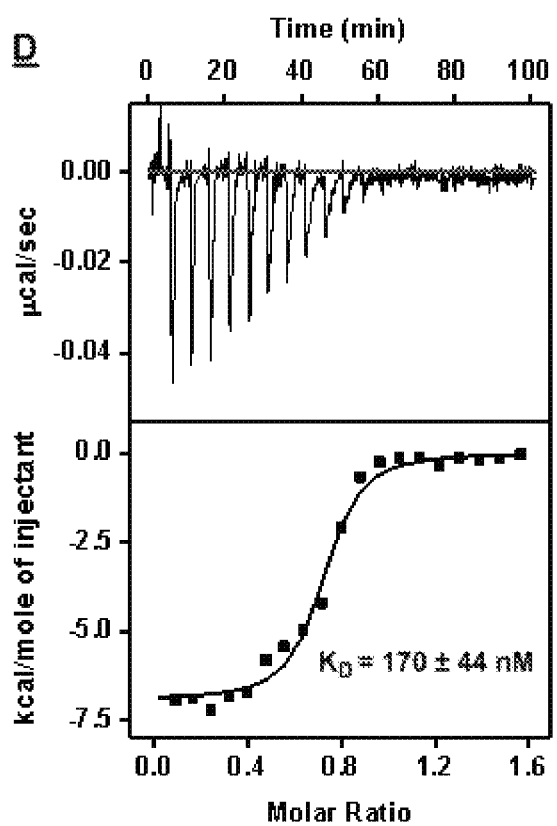

XA1 and XA2 were synthesized and their binding affinity to XLR-11 and UR-144 were characterized with isothermal titration calorimetry (ITC). Results show that XA1 bound tightly to XLR-11 and UR-144 with $K_{DS}$ of 310±70 nM and 127±32 nM, respectively. XA2, on the other hand, had weaker target binding affinities, with $K_{DS}$ of 394±93 nM and 170±44 nM to XLR-11 and UR-144, respectively (FIG. 15). This difference in binding affinity between the two aptamers explains the observed change in their population between round 16 and 17 of SELEX.

Figure 16A:
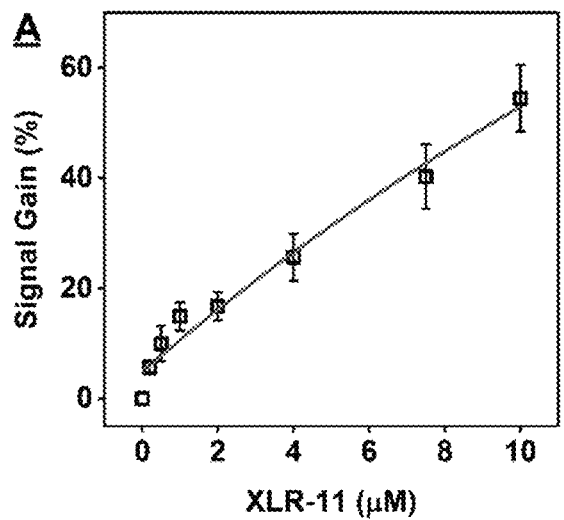
FIGS. 16A-16B show the calibration curve of XA1 for (A) XLR-11 and (B) UR-144 for the strand-displacement fluorescence assay. Concentrations greater than 10 µM were not tested due to the limited solubility of these compounds.
Figure 16B:
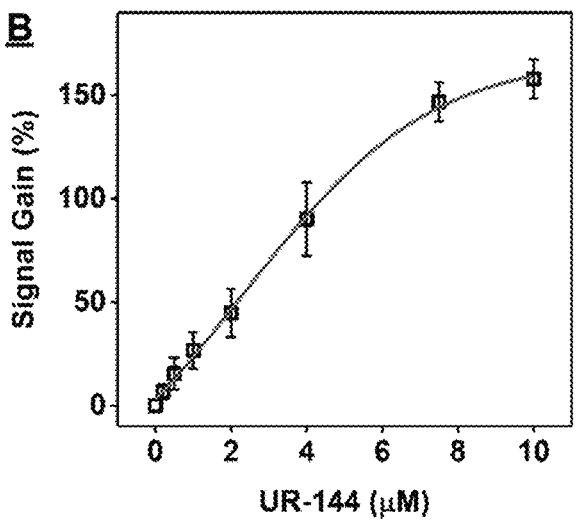
Figure 17:
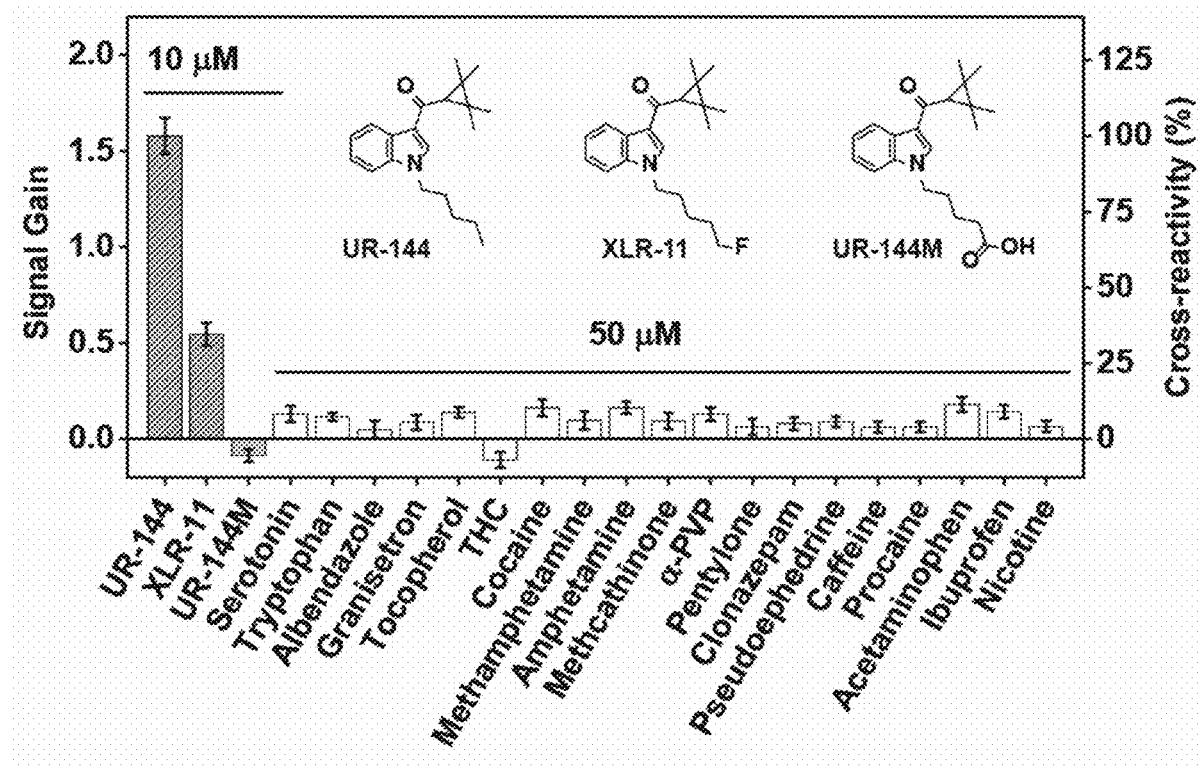
FIG. 17 show the specificity of XA1 for UR-144, XLR-11, and other compounds as determined by the strand-displacement fluorescence assay. Bar plot shows signal gains produced by different compounds and their cross-reactivity relative to UR-144. Inset shows structures of UR-144, XLR-11 and UR-144 pentanoic acid metabolite (UR-144M).

The aforementioned strand-displacement fluorescence assay was also used to characterize the target-binding affinity and specificity of XA1. The results were consistent with ITC data, where XA1 bound to XLR-11 and UR-144 with $K_E$, of 293 nM and 164 nM (FIGS. 14D-E), respectively. Due to the high affinity of the aptamer, as low as 200 nM of XLR-11 or 1 µM of UR-144 can be easily detected using the fluorescence assay (FIG. 16). The detection limits were unimpressive due to competition of the cDNA employed in the assay with the target for binding to the aptamer. Although XA1 can bind both targets with sub micromolar affinity, the major metabolite of UR-144, UR-144 N-pentanoic acid, yielded no signal response in the fluorescence assay. This shows that the addition of a carboxylate group to the alkyl tail of the target impairs binding, making the aptamer very specific to parent drug. Meanwhile, XA1 was very specific and showed minimal cross-reactivity to interferents at a five-fold higher concentration relative to the targets (FIG. 17). Once again, the results showed that aptamers with high target-affinity and specificity can be generated from unmodified DNA libraries against challenging hydrophobic small molecules via SELEX.

Example 5—Naked-Eye Detection of THC and THC-COOH Using a Dye-Displacement Assay The dye 3,3-di(3-sulfopropyl)-4,5,4,5-dibenzo-9-ethylthiacarbocyanine (ETC) binds to THC1.2 as a monomer with absorption maxima at 575 nm. The binding of THC to the aptamer-dye complex caused the displacement of the dye from the aptamer, resulting in J-aggregates which absorb at 660 nm. Based on the difference between the area under the curve of the monomer (500-620 nm) and aggregate peak (620-680 nm) (FIG. 18A) with and without target, THC concentrations were quantified from 0.25 µM to 20 µM (FIG. 18B). This dye-displacement assay also displayed high specificity against structurally similar interferents including CBD and CBG at 5-fold higher concentrations and other drugs and adulterants like cocaine, amphetamine, fentanyl, heroin, procaine, nicotine, and caffeine at 20-fold higher concentrations (FIG. 18C). Importantly, as low as 3 µM THC and THC-COOH can be detected via a purple-to-blue color change visible to the naked eye, with no color occurring in the presence of THCA, CBD, CBG, UR-144, cocaine, methamphetamine, heroin, fentanyl, nicotine, and caffeine (FIG. 18C). Given the high sensitivity and specificity of this assay, as well as its ease of use and second-scale turnaround time, it would be highly amenable for on-site THC and THC-COOH detection.

In summary, aptamers binding to challenging, highly hydrophobic small-molecules with very few functional groups can be directly isolated from natural DNA libraries through SELEX. The THC-binding aptamer (THC1.2) of the subject invention has high target-binding affinity and the ability to bind the metabolite THC-COOH with high specificity against many structurally-similar interferents, particularly the phytocannabinoids CBD and CBG. Notably, this aptamer was isolated with one trial of SELEX, which indicates that the difficulty underlying the isolation of aptamers for THC is related more to the choice of selection conditions rather than the chemical nature of the library or target.

Moreover, the natural DNA libraries can be used to successfully isolate an aptamer binding to two highly hydrophobic, 'low epitope targets', UR-144 and XLR-11. Similar to THC1.2, the isolated aptamer showed nanomolar target-binding affinity and high target specificity. The initial failures in the isolation process were attributable to the selection conditions, in particular, the presence of surfactant in the selection buffer and over-enrichment of non-specific binders (such as THC binders) was deleterious for this SELEX experiment.

As a whole, these results highlight the ligand-binding capability of natural nucleic acids and the great influence that other factors have on the success of in vitro selection. Given the very limited success of modified libraries for the isolation of small-molecule-binding aptamers, it is better to revisit selection strategies and conditions rather than employing modified libraries when the selection for challenging small-molecule targets is not successful.

---

We claim:

1. An aptamer-based sensor comprising an aptamer, the aptamer comprising a nucleic acid sequence selected from i) SEQ ID No: 9, ii) SEQ II) NO: 24 iii) SEQ ID NO: 25, and iv) sequence sharing at least 95% identity with SEQ ID No: 9, 24 or 25.

2. The aptamer-based sensor according to claim 1, the aptamer being modified by addition of a reporter label.

3. The aptamer-based sensor according to claim 2, the reporter label being a fluorescent dye, electroactive tag, a gold nanoparticle (AuNP), or a fluorescent dye and quencher pair.

4. The aptamer-based sensor according to claim 1, the aptamer comprising a nucleic acid sequence selected from SEQ ID Nos: 3-7.

5. The aptamer-based sensor according to claim 1, the aptamer having a maximal length of 73 nucleotides.

6. The aptamer-based sensor according to claim 1, the aptamer having 47 nucleotides.

7. A method for detecting a natural or synthetic cannabinoid in a sample comprising contacting the sample with the aptamer-based sensor of claim 1, and detecting the natural or synthetic cannabinoid in the sample, the detection of the natural or synthetic cannabinoid comprising measuring a signal generated upon binding of the natural or synthetic cannabinoid to the aptamer-based sensor, the signal being a change in absorbance or fluorescence intensity.

8. The method according to claim 7, the sample being a biological sample or an environmental sample.

9. The method according to claim 8, the biological sample being selected from blood, plasma, urine, tears, and saliva.

10. The method according to claim 7, the natural cannabinoid being THC, metabolite thereof, cannabinol (CBN) or tetrahydrocannabivarin (THCV).

11. The method according to claim 7, the synthetic cannabinoid being XLR-11 or UR-144.

12. A method for detecting THC and/or a metabolite thereof in a sample comprising contacting the sample with the aptamer-based sensor, the aptamer-based sensor comprising a aptamer that comprises SEQ ID No: 9 or a sequence sharing at least 95% identity with SEQ ID No: 9, and detecting THC and/or a metabolite thereof in the sample.

13. The method according to claim 12, the detection comprising measuring an absorbance or fluorescence intensity change upon binding of THC and/or a metabolite thereof to the aptamer, or observing a color change by the naked eye.

14. The method according to claim 12, the aptamer comprising a nucleic acid sequence selected from SEQ ID Nos: 3, 6 and 9.

15. The method according to claim 12, the aptamer-based sensor further comprising a complementary nucleic acid sequence, the complementary nucleic acid sequence comprising SEQ ID No: 8.

16. A method for detecting XLR-11 and/or UR-144 in a sample comprising contacting the sample with the aptamer-based sensor, the aptamer-based sensor comprising a aptamer that comprises a nucleic acid sequence selected from SEQ ID Nos: 24-25 and a sequences sharing at least 95% identity with SEQ ID No: 24 or 25, and detecting XLR-11 and/or UR-144 in the sample, the detection comprising measuring a signal generated upon binding of XLR-11 and/or UR-144 to the aptamer, the signal being a change in absorbance or fluorescence intensity.

17. The method according to claim 16, the aptamer comprising a nucleic acid sequence selected from SEQ ID Nos: 4-5 and 7.

* * * * *